(12) United States Patent
Annunziata et al.

(10) Patent No.: US 9,700,449 B1
(45) Date of Patent: Jul. 11, 2017

(54) IMPLANTABLE WEIGHT CONTROL DEVICE TO PROMOTE EARLY AND PROLONGED SATIETY IN A BARIATRIC PATIENT

(71) Applicant: AGT INC., Rancho Mirage, CA (US)

(72) Inventors: Gary Annunziata, Rancho Mirage, CA (US); Timothy Stippick, Phoenix, AZ (US)

(73) Assignee: AGT Inc., Rancho Mirage, CA (US)

( * ) Notice: Subject to any disclaimer, the term of this patent is extended or adjusted under 35 U.S.C. 154(b) by 0 days.

(21) Appl. No.: 15/406,448

(22) Filed: Jan. 13, 2017

Related U.S. Application Data

(60) Provisional application No. 62/278,248, filed on Jan. 13, 2016.

(51) Int. Cl.
*A61M 5/00* (2006.01)
*A61F 5/00* (2006.01)

(52) U.S. Cl.
CPC ............ *A61F 5/0076* (2013.01); *A61F 5/003* (2013.01); *A61F 5/0033* (2013.01); *A61F 5/0079* (2013.01)

(58) Field of Classification Search
CPC ........ A61F 5/003; A61F 5/033; A61F 5/0076; A61F 5/0079
See application file for complete search history.

(56) References Cited

U.S. PATENT DOCUMENTS

| | | | | |
|---|---|---|---|---|
| 7,931,693 | B2* | 4/2011 | Binmoeller | A61F 5/003 606/191 |
| 2005/0273060 | A1* | 12/2005 | Levy | A61B 17/1114 604/192 |
| 2006/0020278 | A1* | 1/2006 | Burnett | A61B 5/14539 606/153 |
| 2008/0208239 | A1* | 8/2008 | Annunziata | A61F 5/0079 606/191 |
| 2015/0209168 | A1* | 7/2015 | Arnholt | A61F 5/003 606/192 |

* cited by examiner

*Primary Examiner* — Leslie Deak
(74) *Attorney, Agent, or Firm* — McDermott Will & Emery LLP

(57) ABSTRACT

The present disclosure provides an inflatable weight control device that is implanted long-term with an endoscope in obese and bariatric human patients to promote early and prolonged satiety. The device includes a flexible member coupled to a valve body assembly and an elongated durable module residing within the flexible member. The flexible member is selectively inflated to form two bulbs with a central passageway extending through the bulbs and the valve body assembly. Once the bulbs are inflated, the device is retained within the patient's pyloric valve to form a gastric outlet obstruction wherein chyme accumulates and then is directed through the central passageway to reach the patient's duodenum. Due to its unique configuration, the implanted device reduces gastric outflow which results in early and prolonged satiety when the patient consumes normal-sized meals or food portions, thereby reducing food consumption and increasing the patient's weight loss.

23 Claims, 22 Drawing Sheets

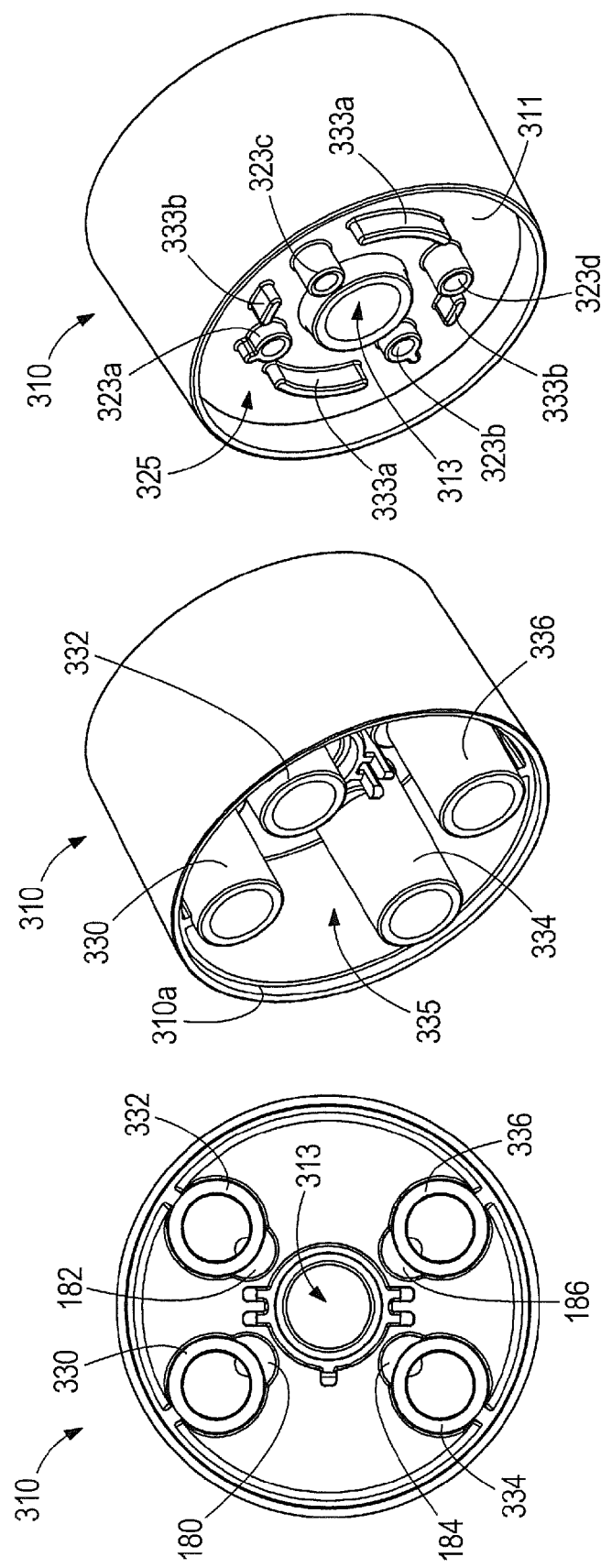

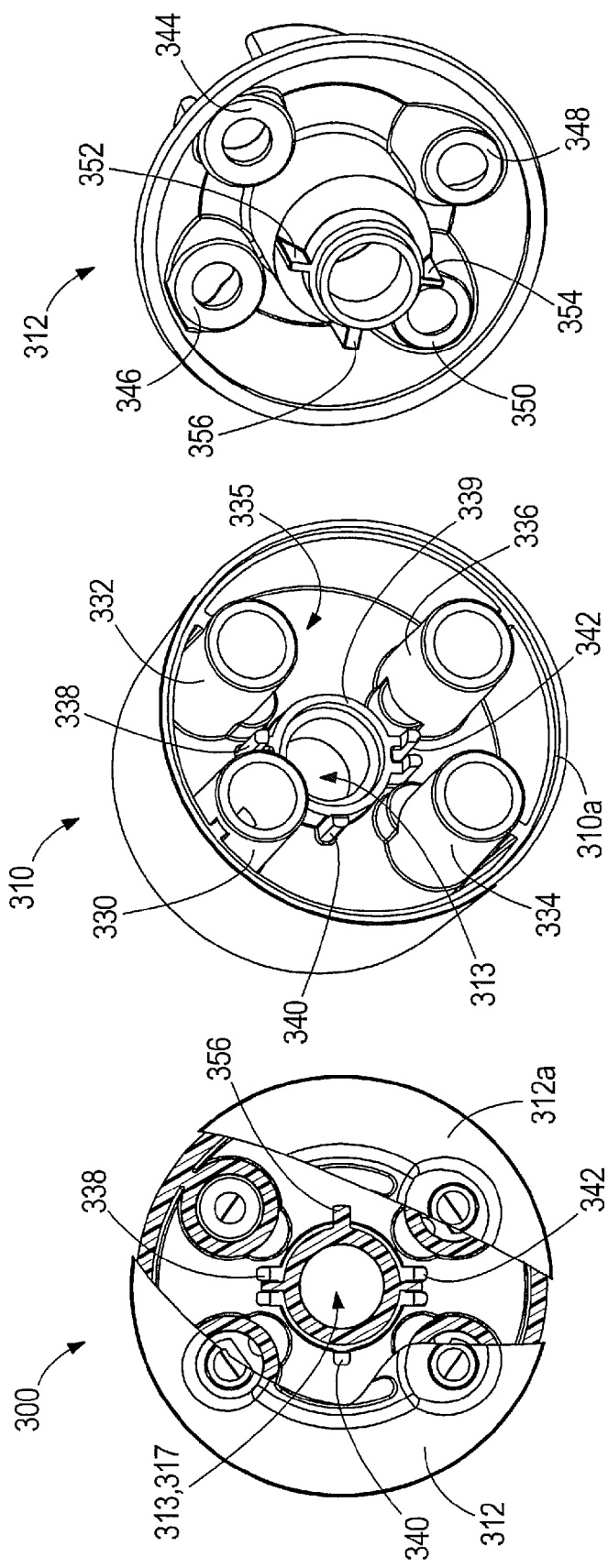

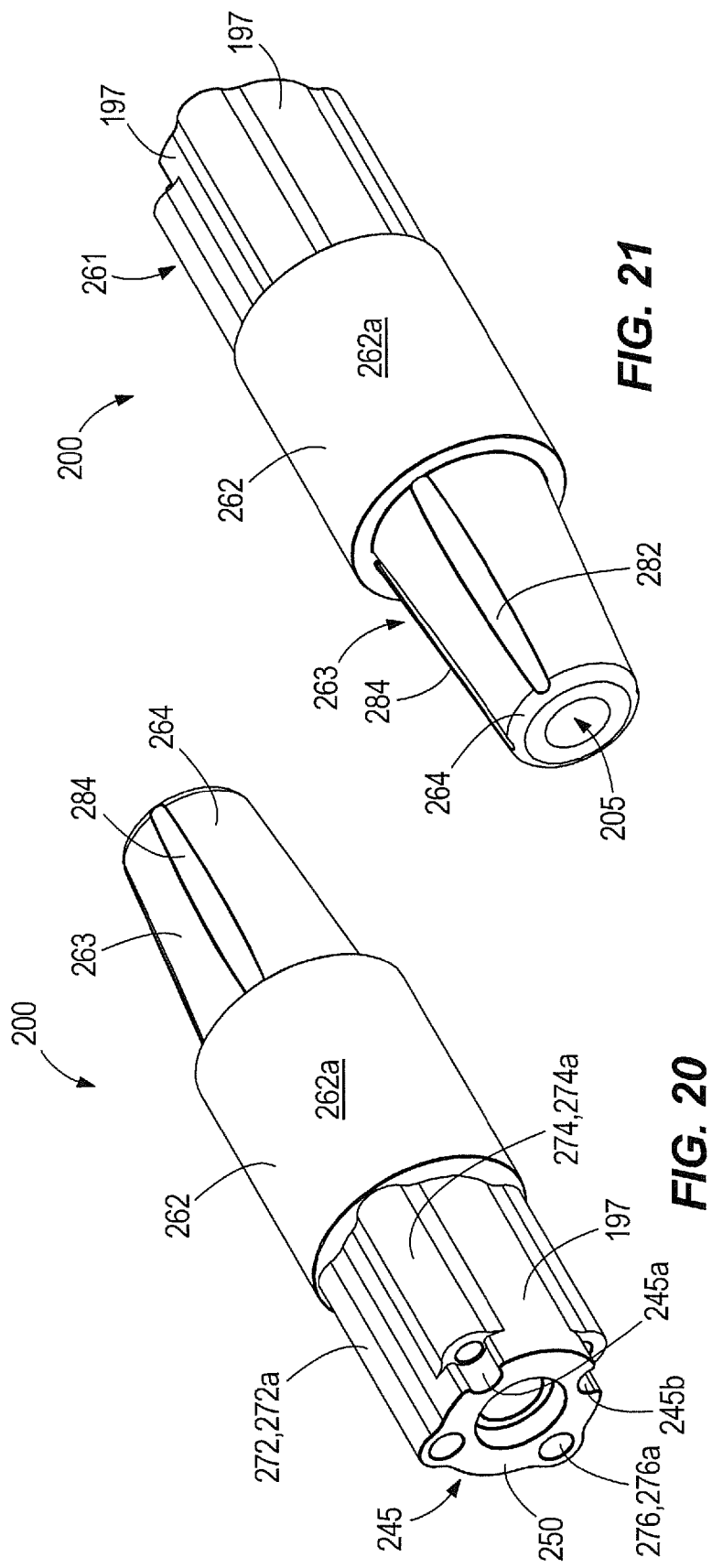

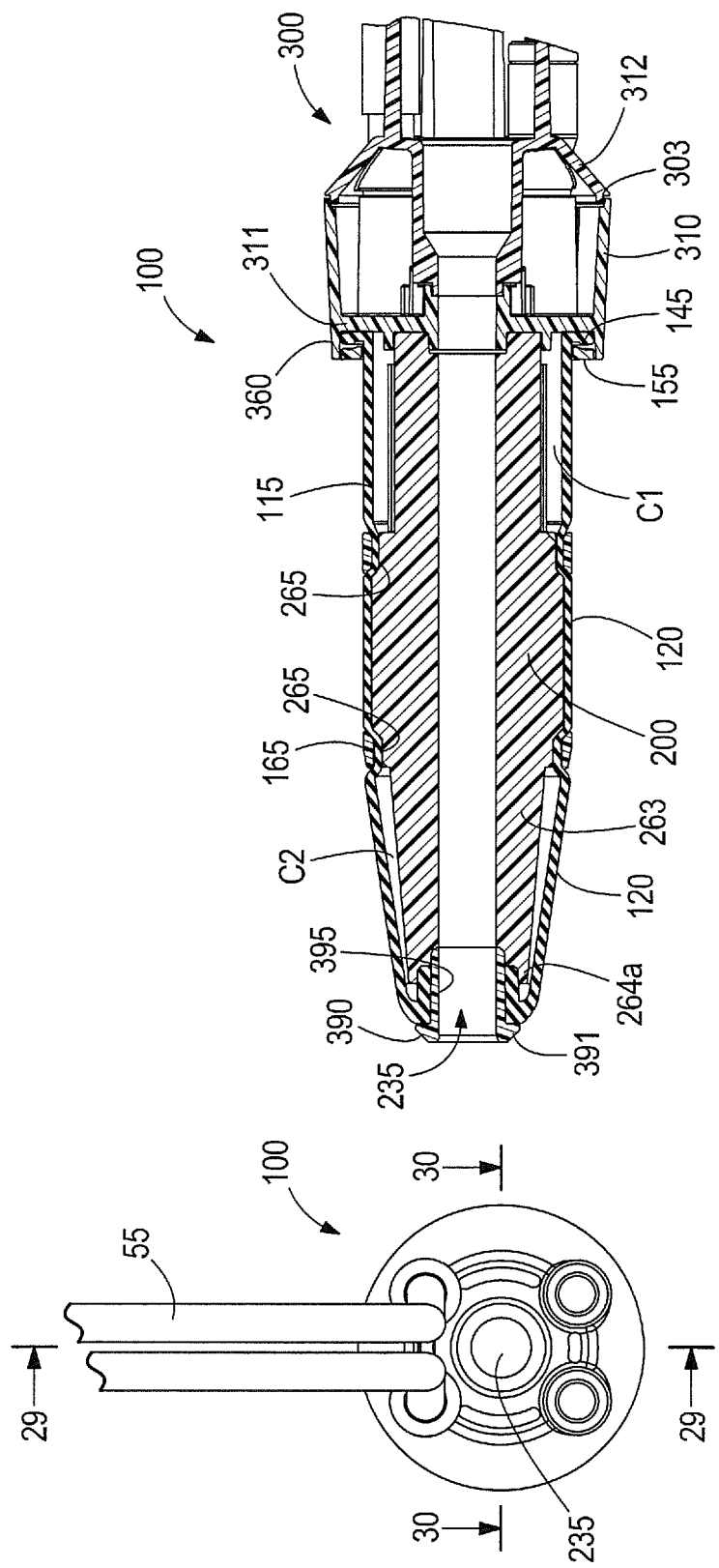

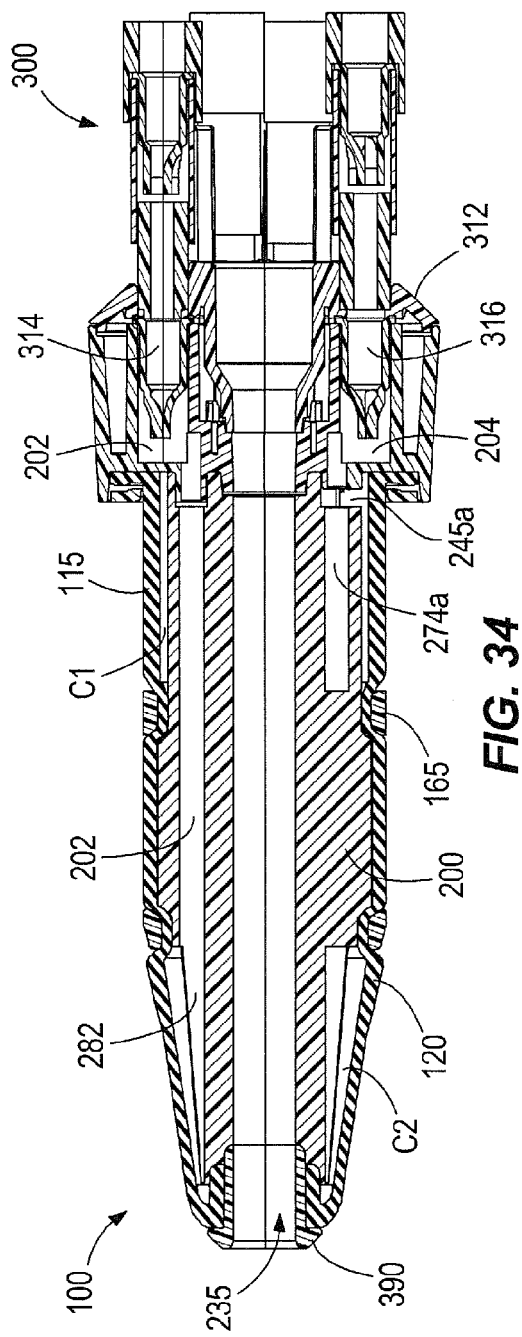
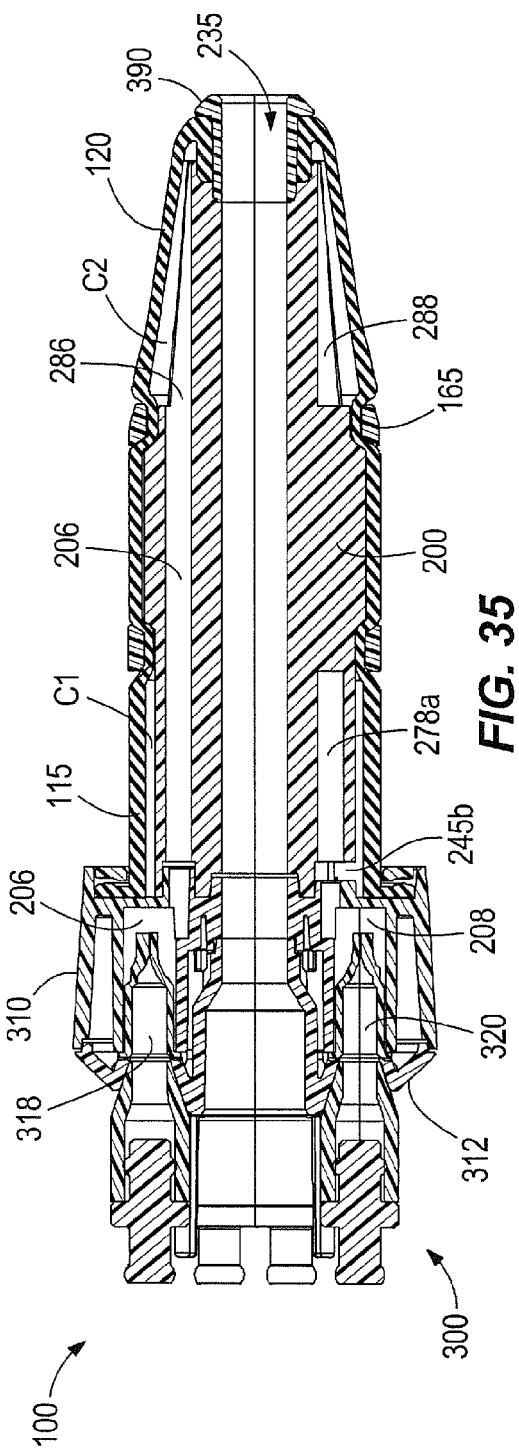
FIG. 34
FIG. 35

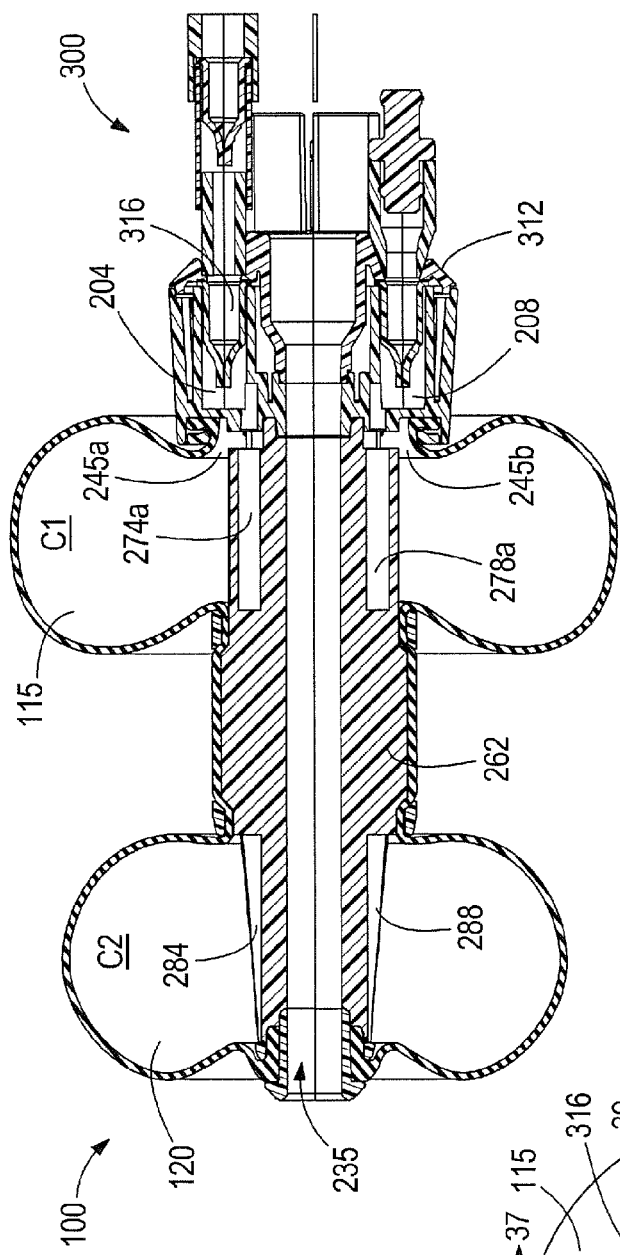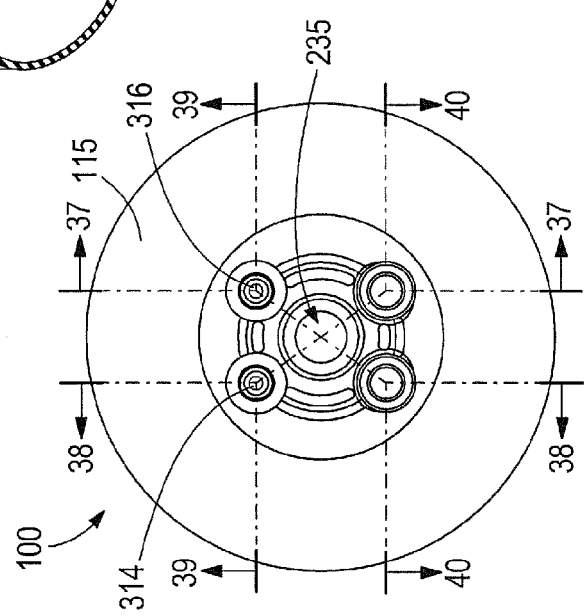

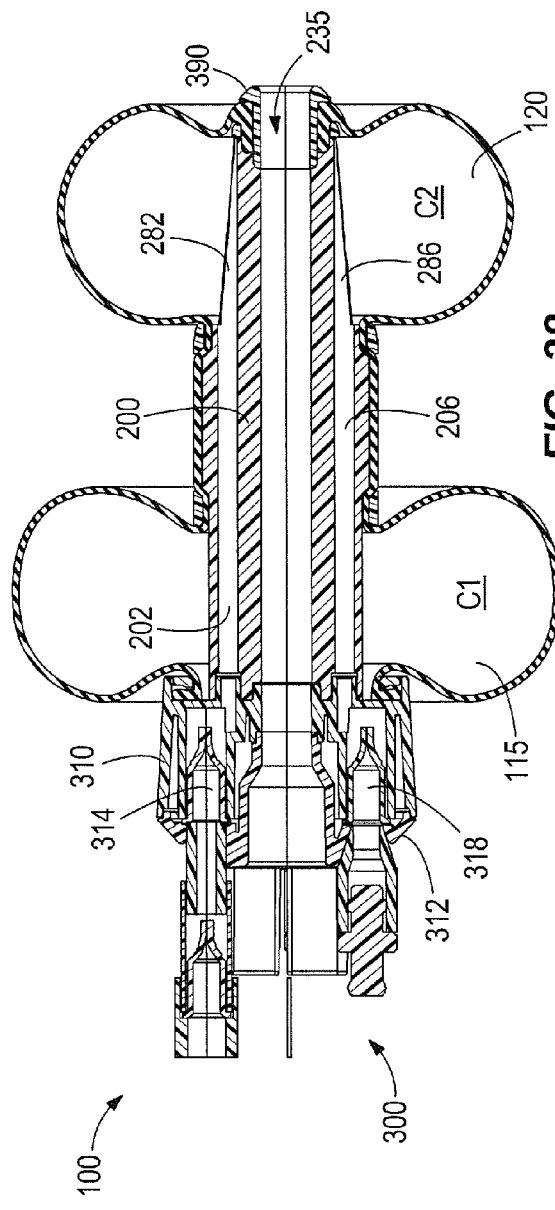
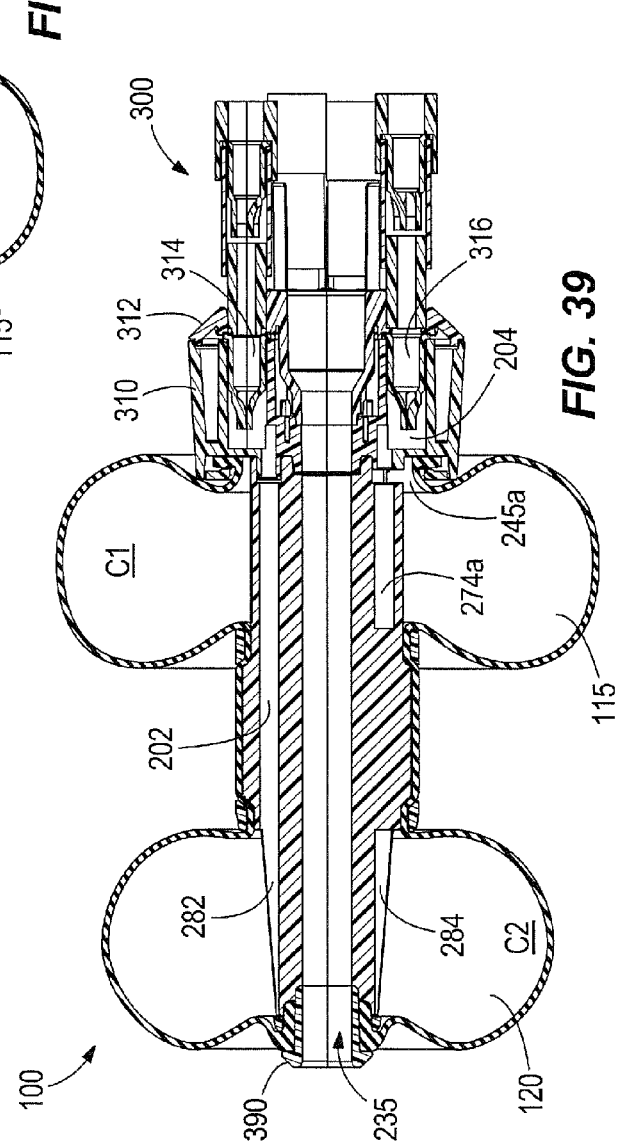

IMPLANTABLE WEIGHT CONTROL DEVICE TO PROMOTE EARLY AND PROLONGED SATIETY IN A BARIATRIC PATIENT

CROSS-REFERENCE TO RELATED APPLICATION

This application claims the benefit of U.S. Provisional Patent Application No. 62/278,248, filed on Jan. 13, 2016 with the United States Patent and Trademark Office, which is expressly incorporated herein by reference and made a part hereof.

TECHNICAL FIELD

The present disclosure provides an inflatable weight control device that is implanted long-term with an endoscope in obese and bariatric human patients to promote early and prolonged satiety, and thus reduce the patient's food intake. The device includes a flexible member coupled to a valve body assembly and an elongated durable module residing within the flexible member. The flexible member is selectively inflated to form two bulbs with a central passageway extending through the bulbs and the valve body assembly. Once the bulbs are inflated, the device is retained within the patient's pyloric valve to form a gastric outlet obstruction wherein chyme accumulates and then is directed through the central passageway to reach the patient's duodenum.

BACKGROUND

It is well recognized that being overweight or obese raises many significant health implications. For example, obesity increases the risk of many diseases and health conditions, including: hypertension, dyslipidemia (for example, high total cholesterol or high levels of triglycerides), type 2 diabetes, coronary heart disease, stroke, gallbladder disease, osteoarthritis, sleep apnea and respiratory problems. In addition to the health implications, overweight and obesity have a significant economic impact on the U.S. health care system. Medical costs associated with obesity involve direct and indirect costs. Direct medical costs include preventive, diagnostic and treatment services related to obesity. Indirect costs relate to morbidity and mortality costs, where morbidity costs are defined as the value of income lost from decreased productivity, restricted activity, absenteeism and bed days, and mortality costs are the value of future income lost by premature death.

Conventional approaches to combat obesity have led doctors to surgically modify patients' anatomies in an attempt to reduce consumption by inducing satiety or a "full" feeling in the patient, thereby reducing their desire to eat. Examples include stomach stapling, or gastroplasties, to reduce the volumetric size of the stomach. In addition, two procedures, the Roux-en-Y gastric bypass and the biliopancreatic diversion with duodenal switch (BPD), reduce the size of the stomach and the effective length of intestine available for nutrient absorption. These two procedures reduce the stomach volume and the ability of a patient to consume food. In an attempt to limit nutrient absorption in the digestive tract, at least one company has introduced a sleeve that is implanted in obese patients. U.S. Pat. No. 7,025,791 discloses a bariatric sleeve that is anchored in the stomach and extends through the pylorus and duodenum and beyond the ligament of Treitz. All chyme exiting the stomach is funneled through the sleeve and bypasses the duodenum and proximal jejunum. By directing the chyme through the sleeve, the digestion and absorption process in the duodenum is interrupted because the chyme cannot mix with the fluids in the duodenum. As there is no mixing of bile with the chyme until the jejunum, the absorption of fats and carbohydrates is reduced. However, these conventional methods suffer from a number of limitations including high correction and mortality rates. Also, conventional methods are costly and prone to adaptation by the patient's digestive tract which reduces the effectiveness of the method.

Accordingly there is a need for an implantable weight loss device that is effective in prompting early and prolonged satiety while being minimally invasive and not irritable to patients over time. At the same time, there is a need to provide a weight control device that can be implanted long-term within a patient with an endoscope in a doctor's office, and that does not require a hospital visit. Finally, it would be advantageous to provide treatment methods for combating obesity based upon the weight loss device that forms a partial gastric outlet obstruction in the stomach to prompt early and prolonged satiety and reduce food consumption.

SUMMARY

The present disclosure provides a weight control device that is implanted and inflated with an endoscope in a patient's digestive track to form a partial gastric outlet obstruction. The weight control device resides within the pylorus and between the duodenum and stomach. The weight control device includes an internal passageway which forms a conduit for the reception and passage of chyme from the stomach through the pylorus and to the duodenum.

According to one or more aspects of the disclosure, the weight control device includes a first inflatable bulb, a second inflatable bulb and an intermediate portion which collectively define an inflatable body. The internal passageway extends through the body, wherein the passageway receives and allows for the passage of chyme from the stomach to the duodenum. In a use position, the first bulb engages an inner surface of the pyloric antrum. This engagement prevents chyme from passing there between and as a result, chyme must pass through the internal passageway to exit the stomach. In the use position, the second bulb engages an inner surface of the duodenum, wherein the second portion resides in the duodenum adjacent the pyloric valve. Also in the use position, the intermediate portion of the body engages an inner surface of the pyloric valve.

According to one or more aspects of the disclosure, the collapsed body is inserted through the patient's mouth and through both the esophagus and stomach with the endoscope. A filling tube associated with the endoscope supplies fill fluid, which may be oil, saline or another fluid, through the valve and into the body until the device is sufficiently inflated to form the gastric outlet obstruction. To remove an implanted device, the body is deflated, such as by piercing the bulbs, and the endoscope is used to remove the deflated body.

According to exemplary embodiments, the present disclosure provides an endoscopically implantable weight control device that forms a partial gastric outlet obstruction in a patient's digestive tract to promote early and prolonged satiety in the patient. The weight control device includes an elongated internal module having a gastric portion, a tapered duodenal portion with a distal end, and an intermediate portion positioned between the gastric and duodenal portions, the internal module also has a central lumen extending through the gastric, duodenal and intermediate portions. A valve body assembly is connected to a gastric end of the internal module, and the valve body has a central aperture, a first set of an inflation valve and a deflation valve and a second set of an inflation valve and a deflation valve, wherein said first and second sets of valves are arranged radially about the central aperture. An inflatable member receives the internal member and that is joined to only (i) the valve body assembly, (ii) the intermediate portion of the internal module and (iii) the distal end of the internal module. The inflatable member has (i) a major segment that has a linear configuration and that overlies the gastric and intermediate portions of the internal module and (ii) a minor segment that has a tapered configuration and that overlies the duodenal portion of the internal module. When the inflatable member is supplied with a working fluid (i) a gastric bulb is formed in the inflatable member, said gastric bulb resides between the valve body assembly and the intermediate portion of the internal module, and (ii) a duodenal bulb is formed in the inflatable member, said duodenal bulb resides between the intermediate portion of the internal module and the distal end of the internal module. The valve body assembly and the internal module include both a first inflation passageway and a first deflation passageway for the transport of the working fluid to the gastric bulb, wherein the gastric bulb forms a partial gastric outlet obstruction when the weight control device is implanted in the patient. When the valve body assembly and the internal module include both a second inflation passageway and a second deflation passageway for the transport of the working fluid to the duodenal bulb. The second inflation and deflation passageways are extend through the gastric and intermediate portions of the internal module to reach the duodenal portion of the internal module. The central lumen of the internal module and the central aperture of the valve body assembly are cooperatively aligned to provide an internal passageway extending through the weight control device that receives and allows for the passage of chyme from the patient's stomach through the device to the duodenum.

Other features and advantages of the disclosure will be apparent from the following specification taken in conjunction with the following drawings.

BRIEF DESCRIPTION OF THE DRAWINGS

To understand the present disclosure, it will now be described by way of example, with reference to the accompanying drawings in which:

FIG. 14 is a rear view of a portion of the valve body assembly of FIG. 8;

FIG. 15 is a perspective view of the portion of the valve body assembly of FIG. 14;

FIG. 16 is another perspective view of the portion of the valve body assembly of FIG. 14;

FIG. 17 is a partially cross-sectioned rear view of the valve body assembly of FIG. 8;

FIG. 18 is a perspective view of a portion of the valve body assembly of FIG. 8;

FIG. 19 is a perspective view of a portion of the valve body assembly of FIG. 8;

FIG. 20 is a perspective view of an internal module of a weight control device;

FIG. 21 is a another perspective view of the internal module of FIG. 20;

FIG. 28 is a rear view of the weight control device in a deflated state with a fill tube assembly attached;

FIG. 29 is a sectional view taken along line 29 of FIG. 28;

FIG. 34 is a sectional view taken along line 34 of FIG. 31;

FIG. 35 is a sectional view taken along line 35 of FIG. 31;

FIG. 36 is a rear view of the weight control device in an inflated state;

FIG. 37 is a sectional view taken along line 37 of FIG. 36;

FIG. 38 is a sectional view taken along line 38 of FIG. 36;

FIG. 39 is a sectional view taken along line 39 of FIG. 36; and

DETAILED DESCRIPTION

Figure 1:
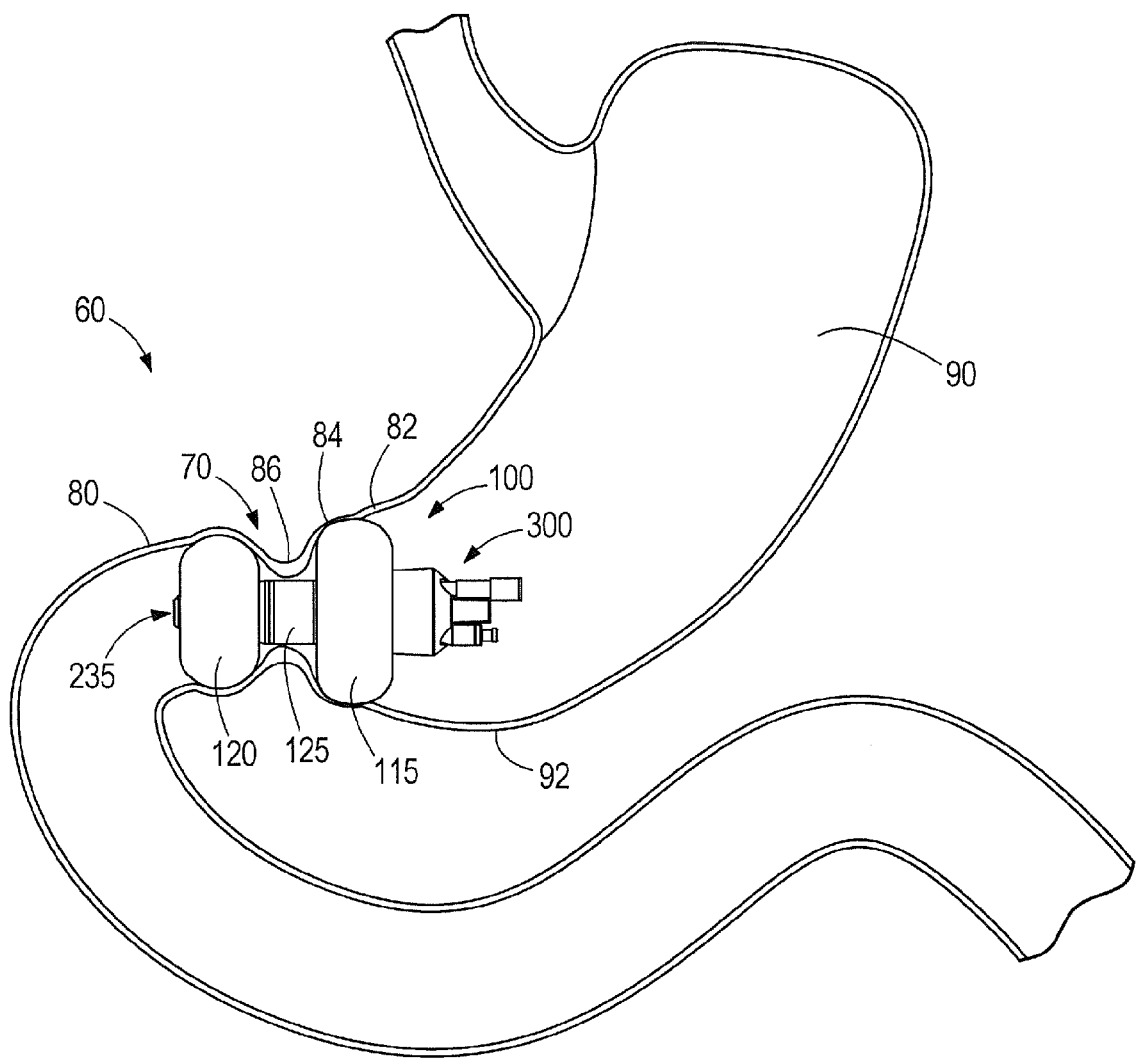
FIG. 1 is an illustration of an inflated weight control device of the disclosure positioned within the digestive tract of a body.

The present disclosure is not intended to be limited to the above-mentioned embodiment. It is easily understood by those of ordinary skilled in the art that there are also various modifications or alternatives without departing from the conception and principle of the present disclosure. The scope of the present disclosure is defined by the appended claims.

FIGS. 1-40 depict one or more embodiments of an inflatable weight control device 100 configured to be implanted in a patient's digestive tract 60 to form a gastric outlet obstruction. An endoscope (not shown) is used to implant the weight control device 100 within the pylorus 70 and between the duodenum 80 and stomach 90 of a patient. The pylorus 70 is the region of the stomach 90 that connects to the duodenum 80 and includes three parts: the pyloric antrum 82, which connects to the body of the stomach 90; the pyloric canal 84, which is downstream of the pyloric antrum 82; and the pyloric sphincter or valve 86, which is a ring of muscle downstream of the pyloric canal 84 that allows for the passage of chyme from the stomach 90 to the duodenum 80.

The weight control device 100 includes a first portion 113 that includes an inflatable first or gastric bulb 115, and a second portion 118 that includes an inflatable second or duodenal bulb 120. The device 100 also includes a number of internal components discussed below that allow for dedicated pairings of inflation and deflation passageways with first and second bulbs 115, 120. In some embodiments, a first pair of inflation and deflation passageways is configured to supply or remove inflation fluid to or from the first bulb 115, while a second pair of inflation and deflation passageways is configured to supply or remove inflation fluid to or from the second bulb 120. As also discussed below, the first and second pairs of inflation and deflation passageways have distinct structures and configurations. As shown in FIG. 1, after inflation the intermediate portion 125 of the weight control device 100 is retained within the pylorus 70 and unintended movement into the duodenum 80 or stomach 90 is prevented. The stomach 90 consists of four coats or layers: the serous coat, the muscular coat, the areolar or sub-mucous coat and the mucous membrane, together with an assortment of vessels and nerves. The weight control device 100 includes an internal central passageway 235 that extends through the first and second portions 113, 118 and which forms a conduit for the reception and passage of chyme from the stomach 90 through the pyloric valve 86 and to the duodenum 80. Chyme is the liquid substance produced in the stomach 90 before passing through the pyloric valve 86 and entering the duodenum 80. Chyme is highly acidic (a pH value of approximately 2) and consists of partially digested food, water, hydrochloric acid and various digestive enzymes. In the absence of the disclosed weight control device 100, chyme passes, unrestricted, from the stomach 90 through the pyloric valve 86 and into the duodenum 80, where the extraction of nutrients begins. The first bulb 115 and the second bulb 120, as well as an entire inflatable member 130, are made from a material suitable for use in the highly acidic environment of the stomach 90.

When the weight control device 100 is implanted and inflated to define an installed or use position (see FIG. 1), an exterior surface of the weight control device 100 engages an inner surface of the pyloric antrum 82. Thus, the first bulb 115 of the weight control device 100 resides between the stomach corpus 92 (the central body portion of the stomach 90) and the pyloric valve 86. As the first bulb 115 is inflatable to various degrees, the dimensions of the first bulb 115 can be customized during inflation to correspond with the dimensions of the pyloric antrum 82 to facilitate engagement between the outer surface of the first bulb 115 and the inner surface of the pyloric antrum 82. In the use position, the device 100 provides three mechanisms for reducing gastric outflow to promote early and prolonged satiety. First, the selectively inflated first bulb 115 nearly seals the pyloric antrum 82 to prevent the normal unimpeded flow of chyme from the patient's stomach 90 into the pylorus 70 and through the pyloric valve 86. This prevention causes chyme to accumulate prior to the pyloric valve 86 whereupon chyme is directed into the internal passageway 235 of the device 100. Second, a small amount of chyme may also migrate around the first bulb 115 and then through the pyloric valve 86 and external to the intermediate portion 125 of the device 100. Third, when the device 100 is properly positioned and inflated, the first bulb 115 reduces the volumetric capacity of the stomach 90. Accordingly, the device 100 has three modes of forming a gastric outlet obstruction that reduces gastric outflow thereby causing the patient to feel satiated or "full" sooner when consuming food. Because the patient will feel satiated sooner or earlier, the patient will consume a reduced amount of food as compared to when he/she consumed same amount and type of food without the device 100 being implanted. Due to the device's 100 unique configuration, including the arrangement of the bulbs 115, 120 and the internal central passageway 235, chyme takes an extended period of time to pass through the device 100 and into the patient's duodenum 80, as compared to the passage of chyme when the device is not implanted in that same patient. Therefore, when the device 100 is implanted, the patient experiences reduced gastric outflow that leads to both early and prolonged satiety. As the device 100 provides three modes of forming the gastric outlet obstruction, the patient will also experience prolonged satiety when he/she consumes normal-sized meals or food portions. For an average sized American male, a normal-sized dinner portion comprises approximately 6 ounces of protein, 1 cup or 6-8 ounces of rice, and 3-4 ounces of vegetables. The early and prolonged aspects of satiety provided by the device 100 reduce the patient's food consumption and increase weight loss in the patient in which the device 100 is implanted.

In the use position, the engagement between the first bulb 115 and the pyloric antrum 82 retains the weight control device 100 in the use position such that the properly inflated first bulb 115 cannot pass beyond the pyloric valve 86 and into the duodenum 80. Thus, the weight control device 100 impairs the flow of chyme and debris during the patient's "fed state" from exiting the stomach 90, causing satiety and thereby reducing the patient's desire or ability to consume more food. Also in the use position, an exterior surface of the second bulb 120 of the weight control device 100 engages an inner surface of the duodenum 80, wherein the second bulb 120 resides in the duodenum 80 downstream of the pyloric valve 86. The engagement between the second bulb 120 and the duodenum 80 retains the weight control device 100 in the use position such that the properly inflated second bulb 120 cannot pass through the pyloric valve 86 and into the pyloric antrum 82 or stomach corpus 92. The orientation of the device 100, including the second bulb 120, ensures that chyme discharged from the internal passageway 235 is directed into the duodenum 80. In the unlikely event that the device 100 is somehow migrates from the pylorus 70 and into the duodenum 80, a study involving implanting the device 100 in Yucatan pigs shows that the device 100 will pass naturally through the patient's digestive tract 60.

Figure 2:
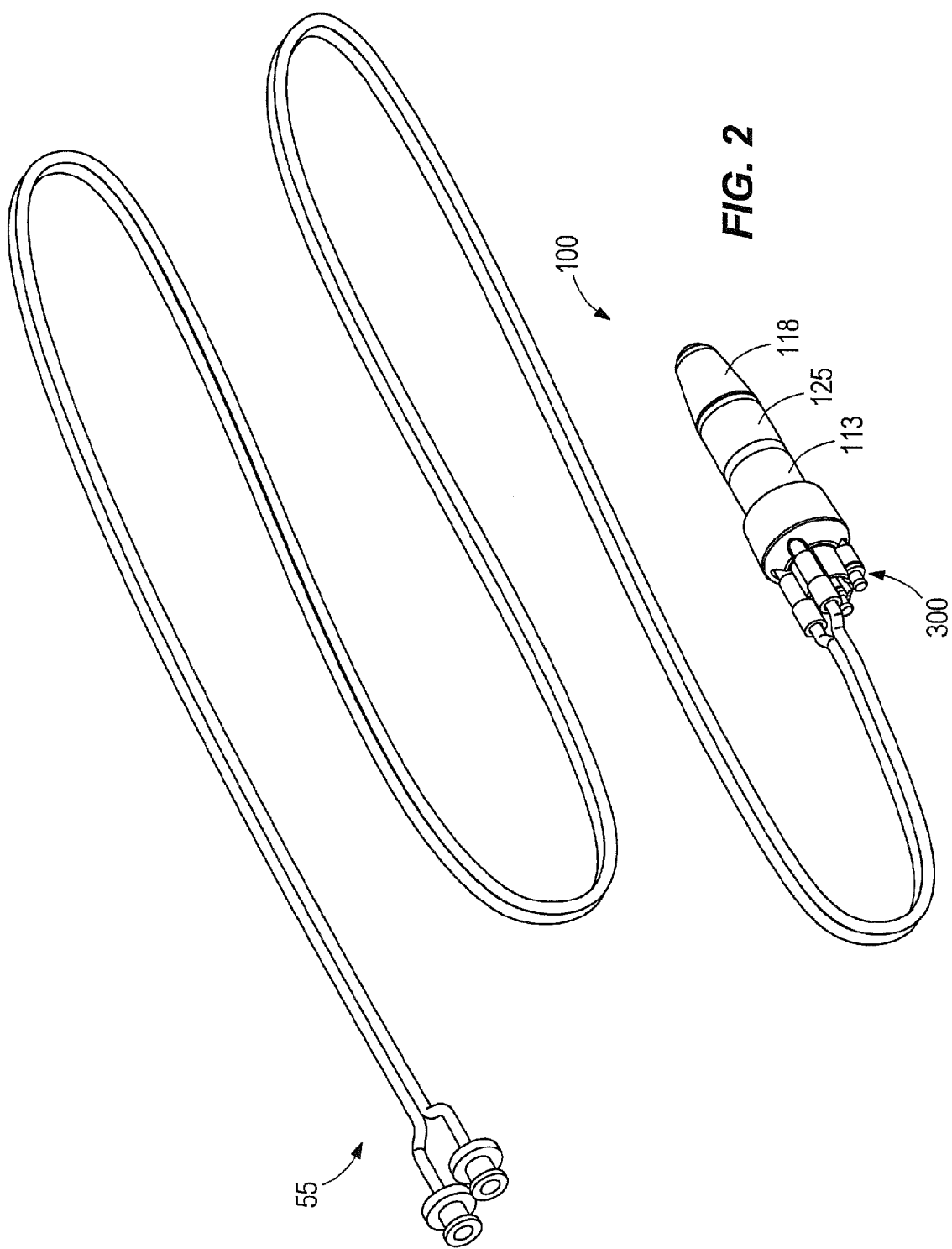
FIG. 2 is a perspective view of a fill tube assembly coupled to the weight control device in a deflated state.
Figure 3:
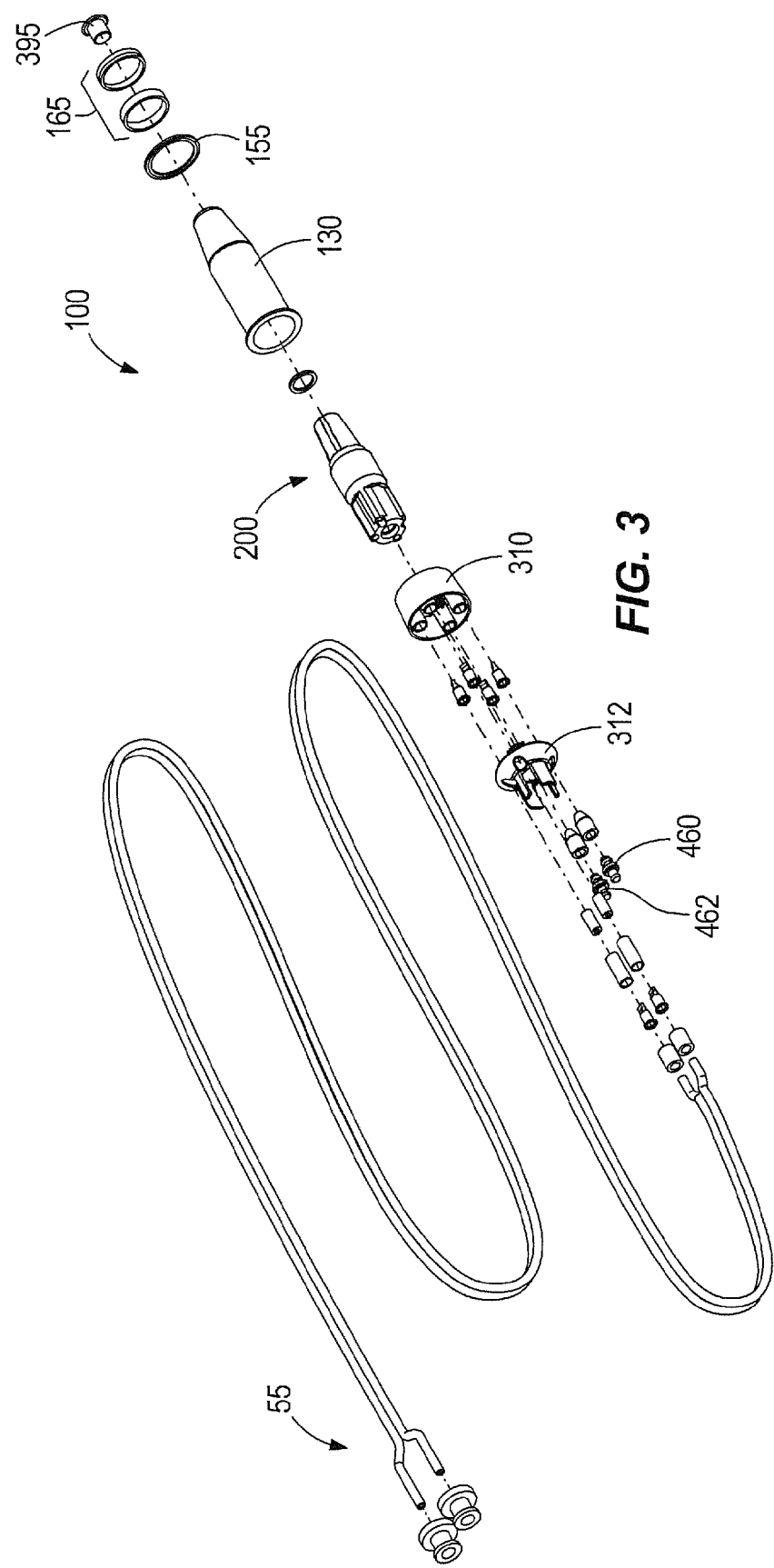
FIG. 3 is an exploded perspective view of the fill tube assembly and weight control device.
Figure 4:
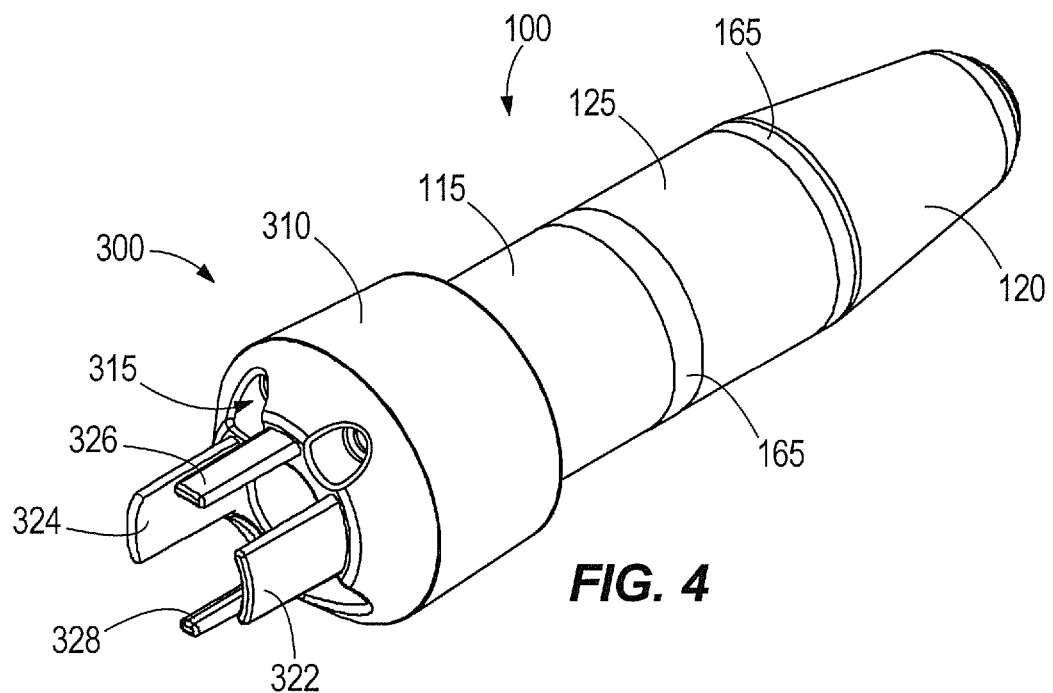
FIG. 4 is a perspective view of the weight control device.
Figure 5:
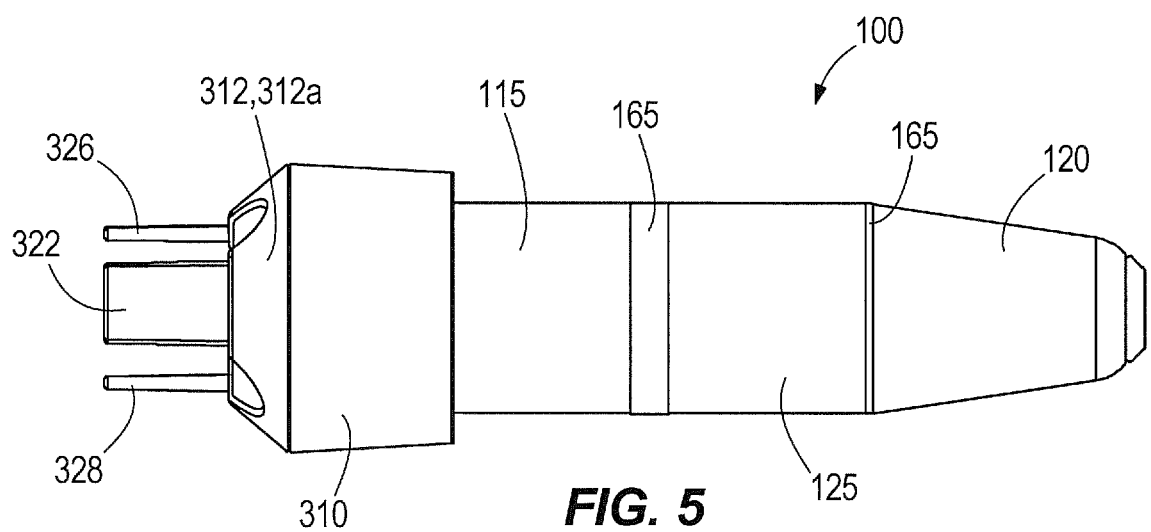
FIG. 5 is a side elevation view of the weight control device.
Figure 6:
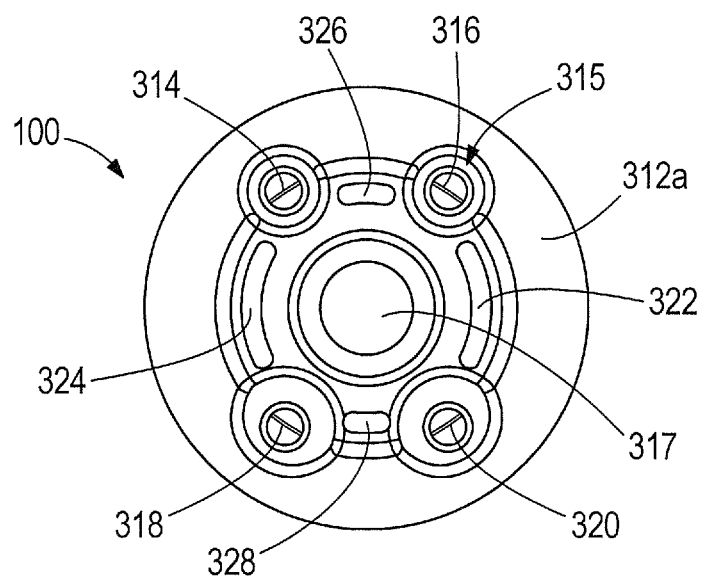
FIG. 6 is a rear view of the weight control device.
Figure 7:
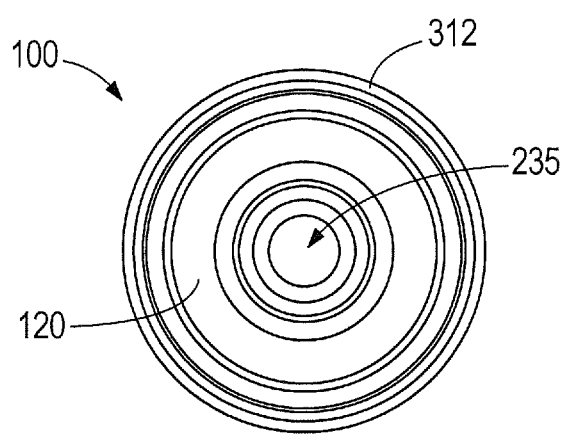
FIG. 7 is a front view of the weight control device.
Figure 8:
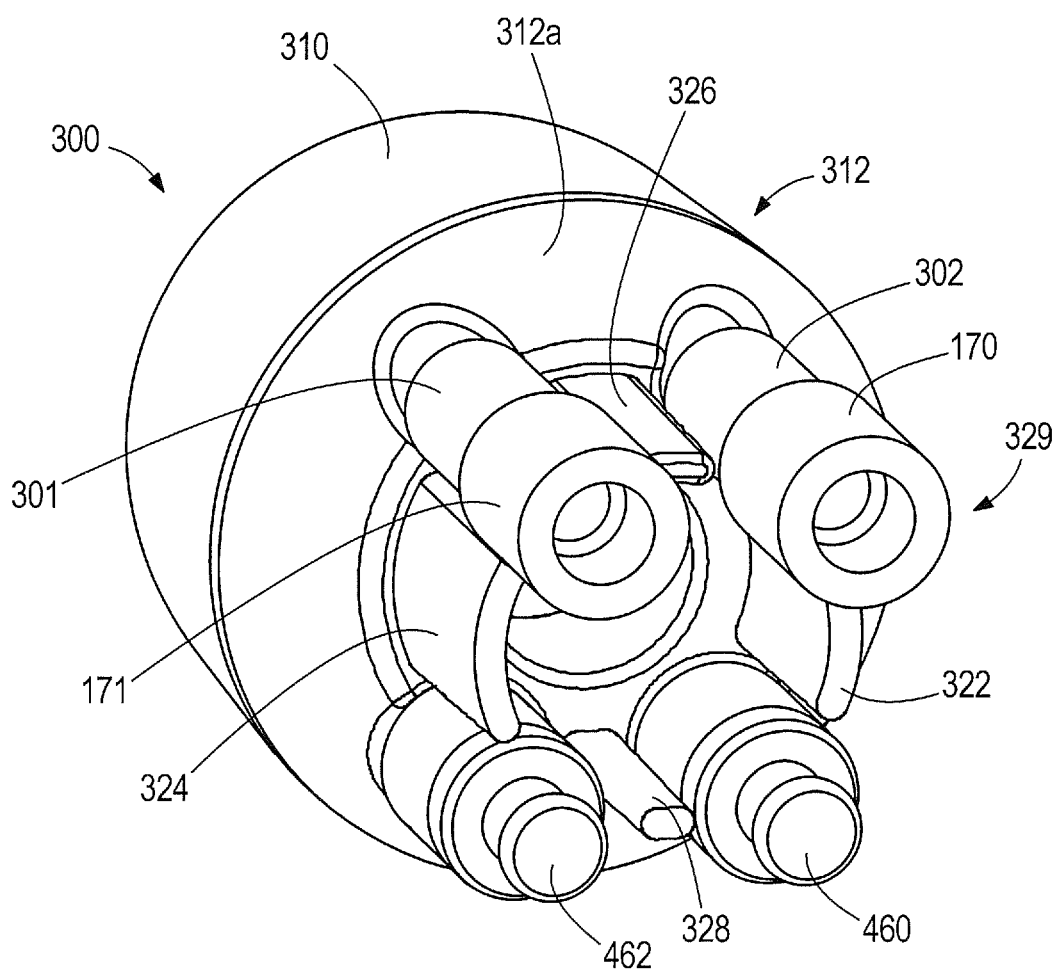
FIG. 8 is a perspective view of a valve body assembly of the weight control device.

FIG. 1 illustrates the weight control device 100 implanted in a patient's digestive tract 60 and inflated to form the gastric outlet obstruction discussed in the foregoing paragraphs. FIGS. 2 and 3 illustrate the weight control device 100 and a fill tube assembly 55 coupled together prior to insertion into a patient. FIGS. 4-7 show various views of the weight control device 100 in a deflated state. Referring to the exploded view of FIG. 3, the weight control device 100 includes an elongated, tubular, flexible bladder or member 130, reinforcing bands 165 that secure the bladder 130 to an internal module 200 residing therein, and a valve body assembly 300. As explained below, the interaction between the bladder 130, the internal module 200 and the valve body assembly 300 lead to the formation of the first and second bulbs 115, 120. The fill tube assembly 55 connects to the valve body assembly 300 to selectively provide inflation fluid to both the first bulb 115 and the second bulb 120 to attain the inflated position of FIG. 1. The first or gastric bulb 115 corresponds to the first portion 113 of the bladder 130, the second or duodenal bulb 120 corresponds to the second portion 118 of the bladder 130, and an intermediate portion 125 is positioned between the first and second bulbs 115, 120. The inflatable member 130, preferably at the intermediate portion 125, is held in place or secured to the internal module 200 by one or more reinforcing bands 165. Thus, the intermediate portion 125 does not inflate and maintains its original diameter. In some embodiments, certain features of the inflatable weight control device 100, including, but not limited to, the inflatable member 130, first bulb 115, second bulb 120 and the internal module 200, have radio-opaque properties enabling them to appear in various medical images, such as those produced by X-rays, computerized tomography and magnetic resonance imaging.

Figure 9:
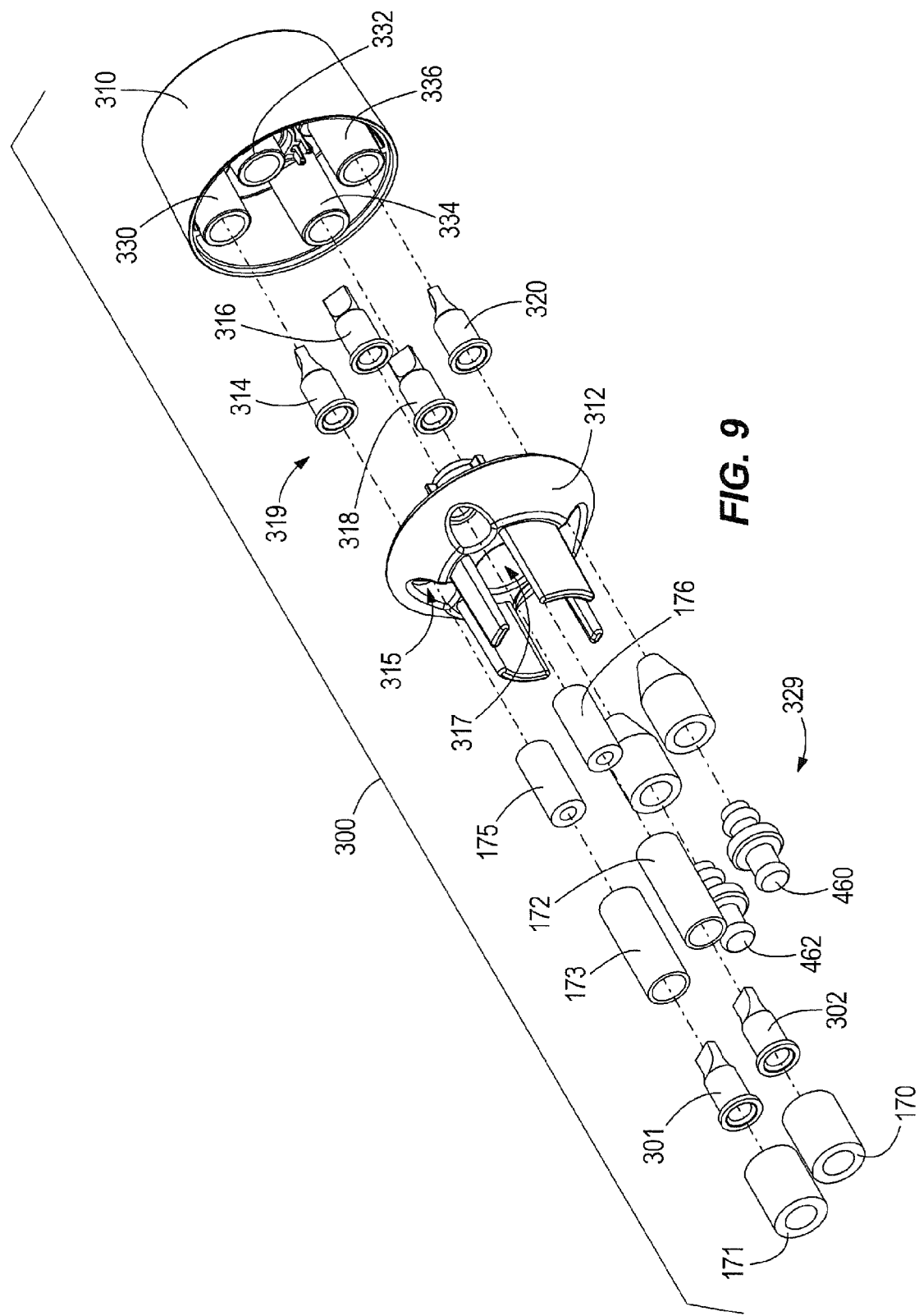
FIG. 9 is an exploded perspective view of the valve body assembly of FIG. 8.

FIGS. 8-19 show various views of portions of the valve body assembly 300. The valve body assembly 300 includes a collar 310 and an end cap 312, an internal valve assembly 319 and an external valve assembly 329. In some embodiments, the internal valve assembly 319 includes a first inflation valve 314, a second inflation valve 316, a first deflation valve 318 and a second deflation valve 320. The valves 314, 316, 318, 320 may be duckbill valves. As shown in FIG. 9, the valves 314, 316, 318, 320 are received by respective valve stems 330, 332, 334, 336 within the collar 310. The collar 310 includes a central collar opening 313 (see FIG. 14) aligned with a lumen 205 of the internal module 200. The end cap 312 has a body portion 312a with a frustoconical configuration and includes apertures 315 arranged about a central end cap opening 317, which is cooperatively aligned with the central collar opening 313. An aperture 315 is cooperatively aligned with a valve 314, 316, 318, 320 received by a valve stem 330, 332, 334, 336. Bushings 315a surround, and/or form, each aperture 315. The end cap 312 additionally has at least one external projection, and preferably a plurality of external projections 322, 324, 326, 328 that extend outwardly from an outer wall of the end cap 312. The projections 322, 324, 326, 328 are configured to be engaged by a medical tool, such as an endoscope, to facilitate insertion or removal of the weight control device 100 into or out of a patient using an endoscope. The projections 322, 324, 326, 328 are arranged radially about the central end cap opening 317 and define a discontinuous pathway to the opening 317. As shown in at least FIGS. 9 and 10, the apertures 315 are positioned at the base of the projections 322, 324, 326, 328 and adjacent the gaps formed between the projections 322, 324, 326, 328. In this manner, the apertures 315 are angularly offset from the projections 322, 324, 326, 328 and adjacent the gaps formed between the projections 322, 324, 326, 328. Preferably, the apertures 315 are positioned radially outward from the projections 322, 324, 326, 328, which are positioned radially outward from the central end cap opening 317.

FIGS. 8-19 show various views of portions of the valve body assembly 300. The valve body assembly 300 includes a collar 310 and an end cap 312, an internal valve assembly 319 and an external valve assembly 329. In some embodiments, the internal valve assembly 319 includes a first inflation valve 314, a second inflation valve 316, a first deflation valve 318 and a second deflation valve 320. The valves 314, 316, 318, 320 may be duckbill valves. As shown in FIG. 9, the valves 314, 316, 318, 320 are received by respective valve stems 330, 332, 334, 336 within the collar 310. The collar 310 includes a central collar opening 313 (see FIG. 14) aligned with the central lumen 205 of the internal module 200. The end cap 312 has a body portion 312a with a frustoconical configuration and includes apertures 315 arranged about a central end cap opening 317, which is cooperatively aligned with the central collar opening 313. An aperture 315 is cooperatively aligned with a valve 314, 316, 318, 320 received by a valve stem 330, 332, 334, 336. The end cap 312 additionally has at least one external projection, and preferably a plurality of external projections 322, 324, 326, 328 that extend outwardly from an outer wall of the end cap 312. The projections 322, 324, 326, 328 are configured to be engaged by a medical tool, such as an endoscope, to facilitate insertion or removal of the weight control device 100 into or out of a patient using an endoscope. The projections 322, 324, 326, 328 are arranged radially about the central end cap opening 317 and define a discontinuous pathway to the opening 317. As shown in at least FIGS. 9 and 10, the apertures 315 are positioned at the base of the projections 322, 324, 326, 328 and adjacent the gaps formed between the projections 322, 324, 326, 328. In this manner, the apertures 315 are angularly offset from the projections 322, 324, 326, 328 and adjacent the gaps formed between the projections 322, 324, 326, 328. Preferably, the apertures 315 are positioned radially outward from the projections 322, 324, 326, 328, which are positioned radially outward from the central end cap opening 317.

Figure 32:
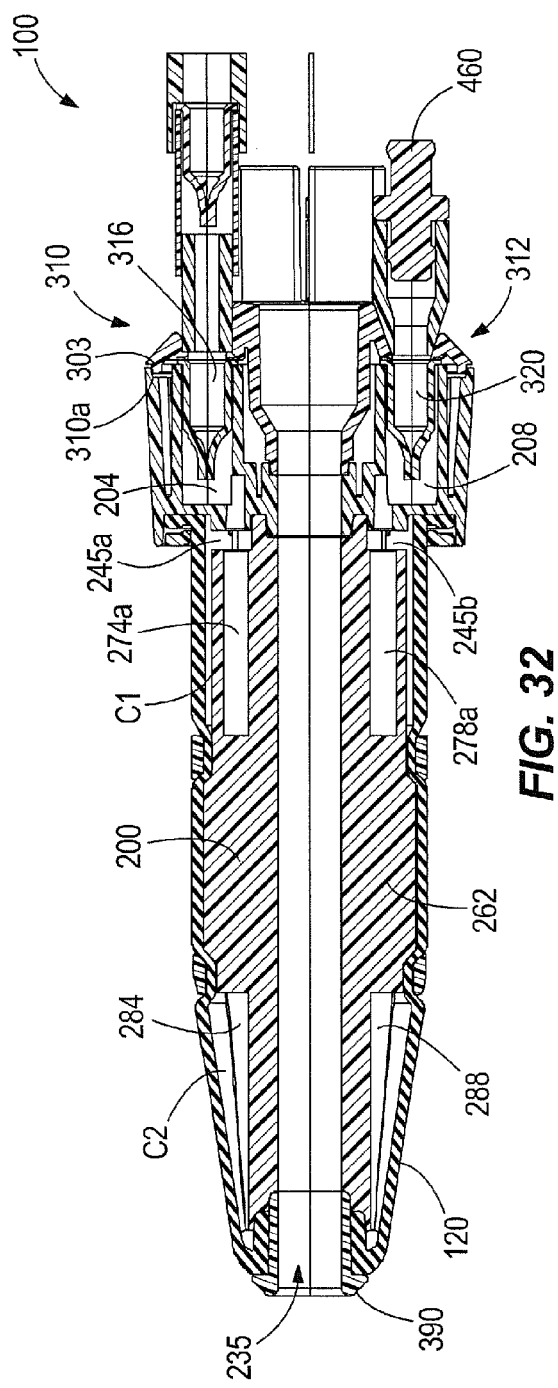
FIG. 32 is a sectional view taken along line 32 of FIG. 31.
Figure 33:
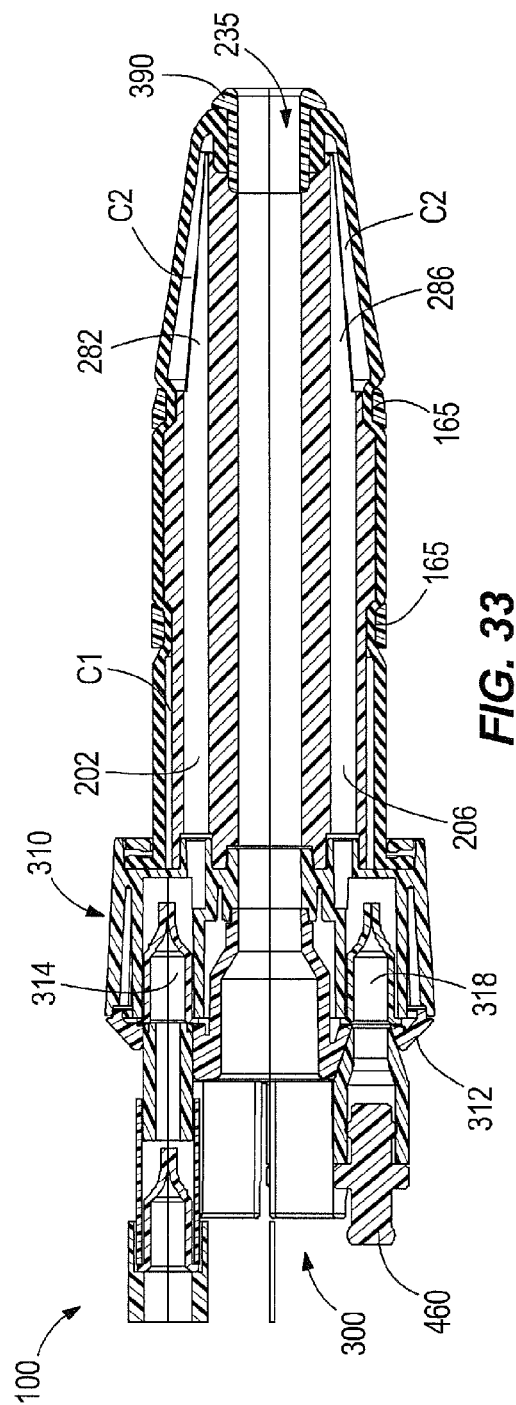
FIG. 33 is a sectional view taken along line 33 of FIG. 31.

FIGS. 14, 32 and 33 illustrate offset flow chambers 180, 182, 184, 186. The offset flow chambers 180, 182, 184, 186 are positioned radially inward from and partially overlap the internal valve stems 330, 332, 334, 336 with respect to the central collar opening 313. The offset flow chambers 180, 182, 184, 186 provide a pathway for working fluid to travel to and from internal valve stems 330, 332, 334, 336, respectively, for purposes of inflating or deflating the first and second bulbs 115, 120. FIG. 16 illustrates flow channels 323a, 323b, 323c, 323d residing within a downstream internal cavity 325 and extending from an inner wall 311 of the collar 310, wherein the flow channels 323a, 323b, 323c, 323d are in fluid communication with offset flow chambers 180, 182, 184, 186, respectively. Together, the offset flow chambers 180, 182, 184, 186, respective internal valve stems 330, 332, 334, 336, and flow channels 323a, 323b, 323c, 323d form portions of the inflation and deflation fluid passageways 202, 204, 206, 208 of the internal module 200. In the embodiment of the Figures, the flow channels 323c, 323d are longer than flow channels 323a, 323b because flow channels 323c, 323d supply working fluid to the duodenal bulb 120, while flow channels 323a, 323b supply working fluid to the gastric bulb 115.

The external valve assembly 329 includes additional components to facilitate the sealing any of apertures 315 (e.g., gaskets, adapters, plugs) and to provide interconnection with the fill tube assembly 55 (e.g., gaskets, adapters, valves). As also shown in FIG. 9, supplementary valves 301 and 302 are, in some embodiments, longitudinally aligned with the first inflation valve 314 and the second inflation valve 316, respectively. Supplementary valves 301, 302 are included in valve body assembly 300 and serve to prevent debris from entering and interfering with operations of the first and second inflation valves 314, 316, respectively, and also prevent a reverse flow of fluid from the inflatable weight control device 100. In addition, valve mount tubes 170, 171, 172, 173, 174, 175, 176 allow the securement of supplementary valves 301, 302 to the inflatable weight control device 100. Some or all of the valve mount tubes 170-176 may use adhesives, a telescopic relationship and/or a press-fit relationship with each other or with the end cap 312 to secure the supplementary valves 301, 302 to the inflatable weight control device.

Figure 10:
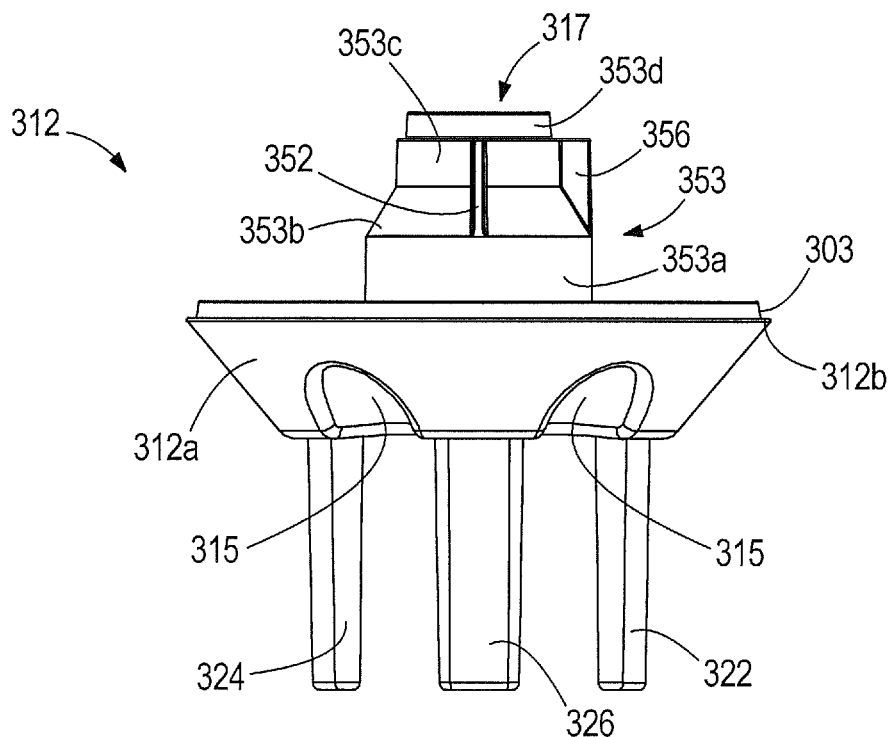
FIG. 10 is a side view of a portion of the valve body assembly of FIG. 8.
Figure 11:
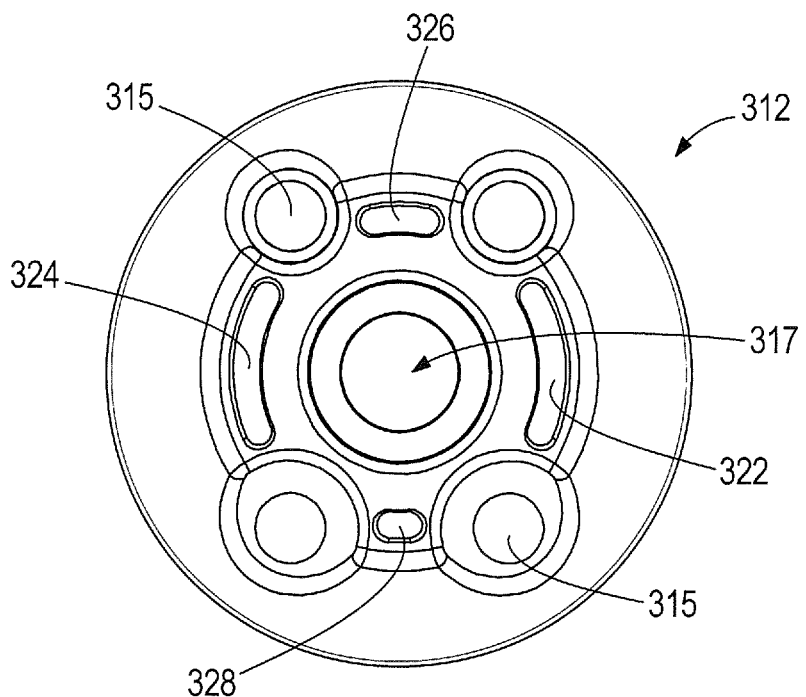
FIG. 11 is a rear view of the portion of the valve body assembly of FIG. 10.
Figure 12:
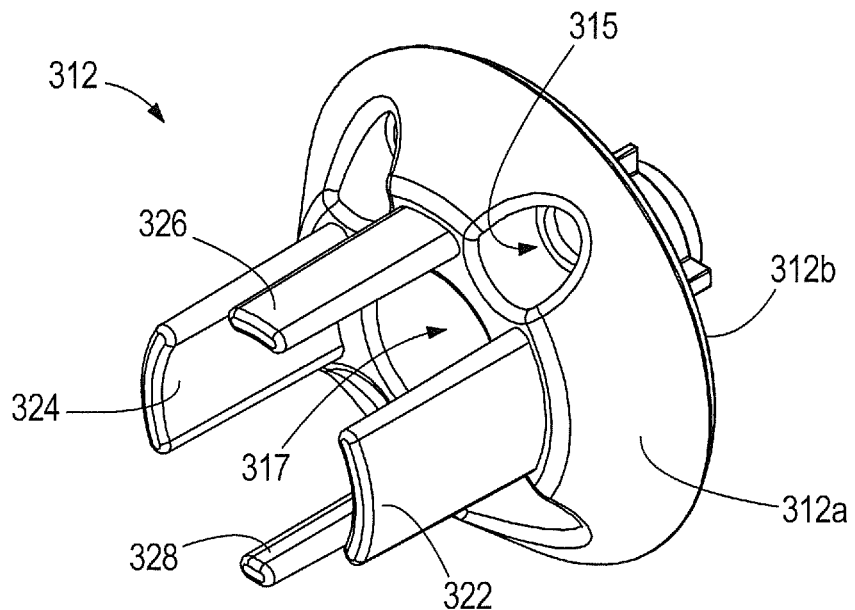
FIG. 12 is a perspective view of the portion of the valve body assembly of FIG. 10.
Figure 13:
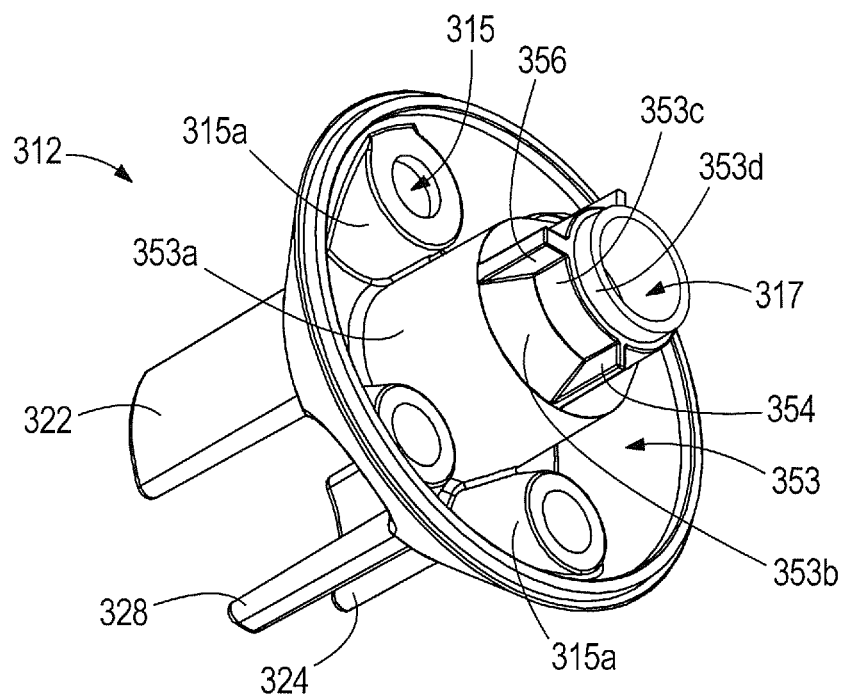
FIG. 13 is another perspective view of the portion of the valve body assembly of FIG. 10.

Referring to FIG. 9, the internal valve stems 330, 332, 334, 336 are generally cylindrical and are adapted to receive the valves 314, 316, 318, 320. As shown in FIG. 18, the internal region of the collar 310 includes an assortment of internal structures to ensure proper orientation and securement of the collar 310 and the end cap 312. The collar 310 includes a first alignment rail receptacle 338, an alignment post 340, and a second alignment rail receptacle 342 affixed to a segmented central boss 339 surrounding the central opening 313. The alignment rail receptacles 338, 342 and the alignment post 340 interact with structures on the internal region of the end cap 312 to ensure proper orientation of the collar 310 with the end cap 312 during assembly of the valve body assembly 300. As shown in FIG. 19, the end cap 312 has a plurality of internal stems 344, 346, 348, 350 that align with and interact with the internal stems 330, 332, 334, 336 of the collar 310 to seal the valves 314, 316, 318, 320 between the collar 310 and the end cap 312 of the valve body assembly 300. The end cap 312 additionally comprises a first alignment rail 352, a second alignment rail 354 and an alignment post 356 extending along an extent of a segmented central bushing 353 surrounding the central opening 317. Referring to FIGS. 10, 13 and 19, the central bushing 353 includes a base portion 353a, a tapered intermediate portion 353b, a linear intermediate portion 353c and an end portion 353d. Preferably, the rails 352, 354 and the post 356 do not extend along the base bushing portion 353, which has a larger diameter than the other portions of the busing 353. Also, the end portion 353d has reduced diameter compared to the intermediate portion 353c wherein a notch is formed at the junction of the end portion 353d and the intermediate portion 353c.

When the device 100 is assembled, the alignment rails 352, 354 of the end cap 312 are received by the alignment rail receptacles 338, 342 of the collar 310 to ensure proper alignment of the collar 310 and the end cap 312 of the valve body assembly 300 while preventing unwanted rotation during assembly. The alignment post 340 and the alignment post 356 are arranged such that upon an incorrect reception of the alignment rails 352, 354 by the alignment rail receptacles 338, 342, or when alignment rail 352 is received by alignment rail receptacle 342 and when alignment rail 354 is received by alignment rail receptacle 338, the alignment posts 340 and 356 interfere with each other, preventing such an orientation of the collar 310 and the end cap 312. Thus, the collar 310 cannot be improperly aligned with the end cap 312 due to the positional relationship of the alignment posts 340 and 356. Proper alignment of the collar 310 and the end cap 312 is imperative because the device 100 includes dedicated inflation and deflation passageways 202, 204, 206, 208 for the first and second bulbs 115, 120, the function of which would be compromised if the collar 310 and the end cap 312 are misaligned. When the collar 310 and the end cap 312 are assembled, a substantial extent of the central bushing 353 projects beyond the peripheral flange 312b of the body portion 312a and into the upstream internal cavity 335 of the collar 312. Preferably the bushing 353 is aligned with the central collar opening 313 and the end portion 353d of the bushing 353 is received by collar opening 313. As illustrated in FIGS. 10, 15, 18 and 32, an end cap groove 303 is positioned radially inward of the peripheral flange 312b and engages with a corresponding collar groove 310a when the end cap 312 mates with the collar 310.

To assemble the valve body assembly 300, the valves 314, 316, 318, 320 are inserted into the internal stems 330, 332, 334, 336 of the collar 310. Adhesive may be used to secure the valves 314, 316, 318, 320 to the internal valve stems 330, 332, 334, 336, but it is also contemplated that a press fit may be utilized. Next, the end cap 312 is rotationally aligned with the collar 310 so that the alignment rails 352, 354 are aligned with the alignment rail receptacles 338, 342. The end cap 312 is then connected to the collar 310, such as by use of an adhesive to form the valve body assembly 300. This coupling of the end cap 312 and the collar 310 brings the central openings 313, 317 into alignment, which results in a central valve body aperture 331 that extends through the collar 310 and the end cap 312 and that functions as a passageway for chyme through the valve body assembly 300. Once the valve body assembly 300 is formed, it may be attached to the internal module 200, such as with an adhesive. The inflatable member 130 and one or more reinforcing bands 165 are attached to the internal module 200 and the valve body assembly 300 as described herein, such as with an adhesive.

Figure 23:
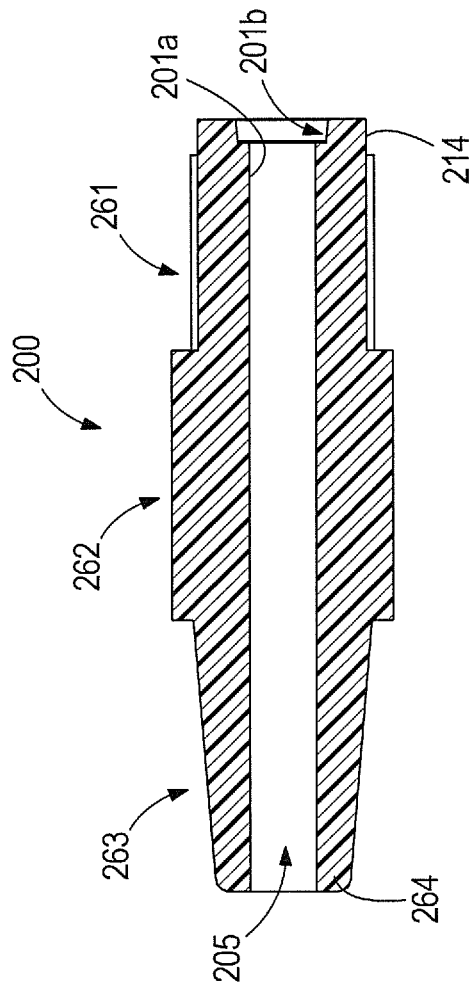
FIG. 23 is a sectional view taken along line 23 of FIG. 22.
Figure 22:
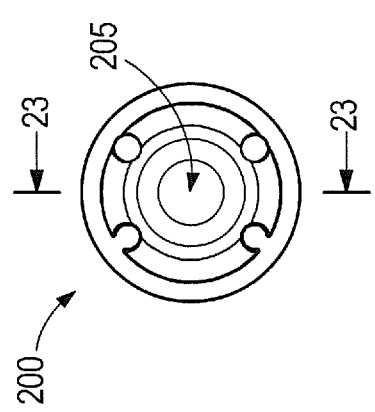
FIG. 22 is a rear view of the internal module of FIG. 20.
Figure 25:
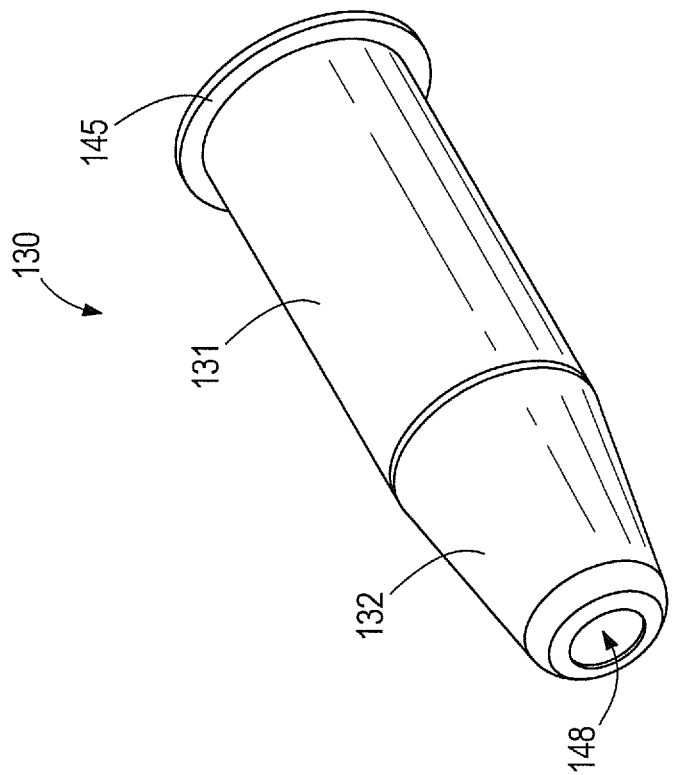
FIG. 25 is another perspective view of the inflatable body of FIG. 24.
Figure 24:
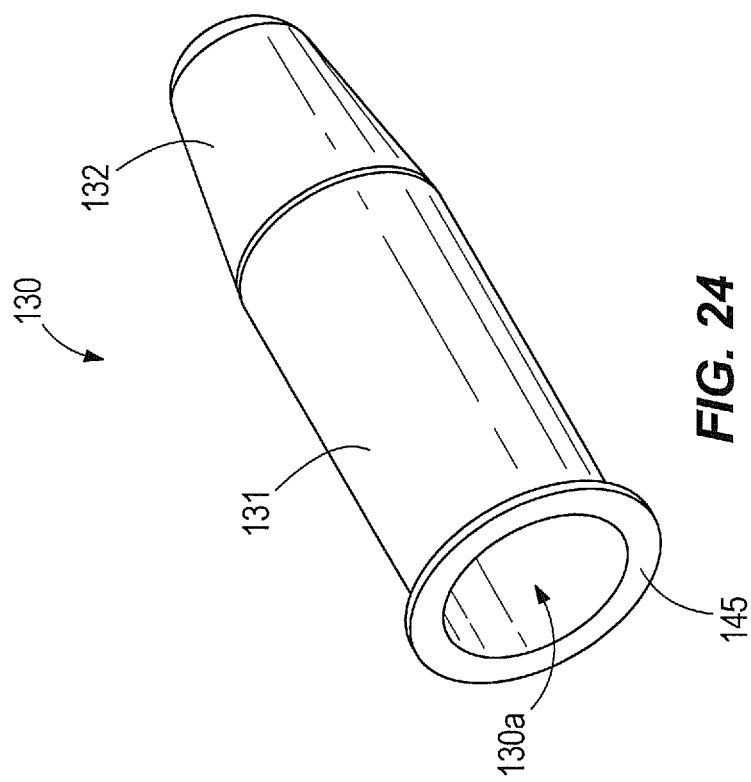
FIG. 24 is a perspective view of an inflatable body of a weight control device.
Figure 30:
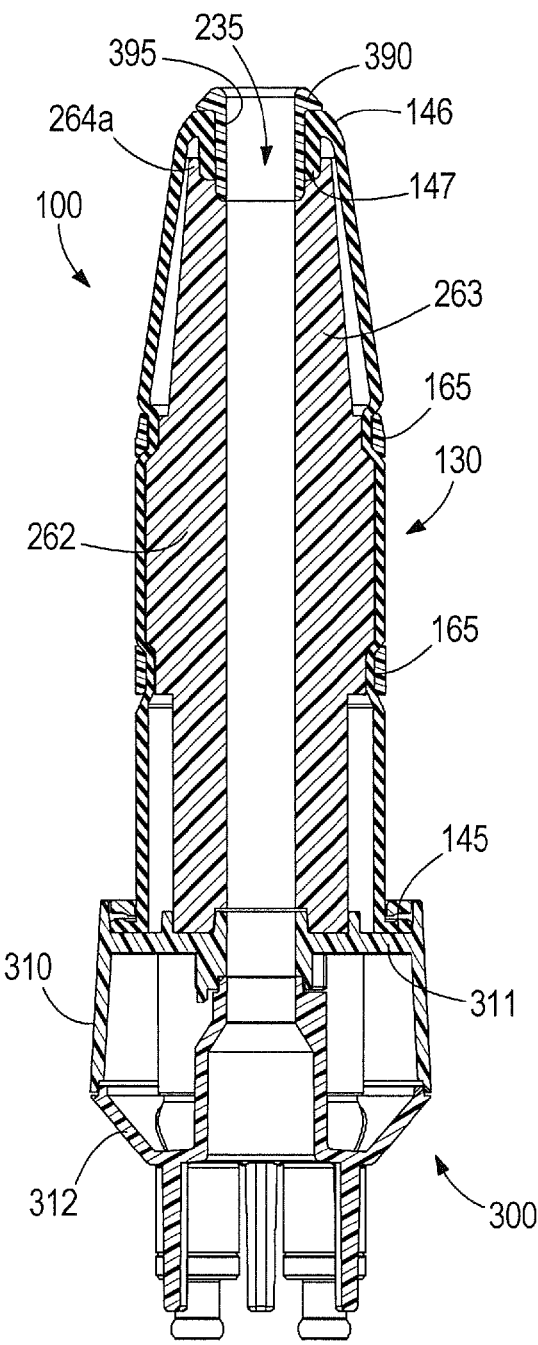
FIG. 30 is a sectional view taken along line 30 of FIG. 28.

FIGS. 20-23 show various views of an internal module 200, which has a substantially rigid construction that minimizes bending, bowing and deformation during implantation of the device 100 in the pylorus 70, as well as subsequent removal of the device 100. The module 200 includes a gastric portion 261, an intermediate portion 262 and a duodenal portion 263 with a duodenal end 264 that is the distal end of the module 200. The module 200 includes an internal central lumen 205 extending between the opposed ends of the module 200 and through the gastric, intermediate and duodenal portions 261, 262, 263. The internal lumen 205 is cooperatively positioned with the distal balloon opening 148, the central collar opening 313 and the central end cap opening 317 to define a central internal passageway 235 that extends through the device 100, including inflatable balloon 130, the internal module 200 and the valve body assembly 300. As device 100 causes chyme to accumulate in the patient's stomach in the region near the valve body assembly 300, the central internal passageway 235 receives, and allows for the passage of, chyme from the patient's stomach through the device 100 and to the duodenum. In the embodiment of the Figures, the gastric portion 261 and the intermediate portion 262 both have a linear outer wall configuration wherein the intermediate portion 262 has a greater outer diameter than the gastric portion 261. As shown in FIGS. 23, 29 and 30, the end of the inner wall 201a of the gastric portion 261 has a reduction in diameter that forms a notched receiver 201b that is configured to receive an extent of the flange 313a that surrounds the central collar opening 313. In one embodiment, other than the notched receiver 201b, the internal lumen 205 has a substantially constant internal diameter along its length and as it extends through the gastric, intermediate and duodenal portions 261, 262, 263. While the internal diameter of the lumen 205 is substantially constant, the duodenal portion 263 has a tapered outer wall configuration leading to the distal end 264.

The internal module 200 also includes a plurality of fluid passageways, namely a first inflation passageway 204, a first deflation passageway 208, a second inflation passageway 202, and a second deflation passageway 206 (see FIGS. 32 and 33). As explained below, the inflation and deflation fluid passageways 202, 204, 206, 208 are configured and positioned to allow for precise inflation and deflation of the first and second bulbs 115, 120. For example, fluid communication ports, or flow channels, 323a-d of the collar 310 (see FIG. 16) are aligned with the inflation and deflation fluid passageways 202, 204, 206, 208 of the internal module 200 by the engagement of alignment members 333a, b of the collar 310 (see FIG. 16) with corresponding portions of the internal module 200. Larger alignment members 333a and smaller alignment members 333b are arranged about the central collar opening 313. Therefore, each of the first and second bulbs 115, 120 are associated with both an inflation passageway and a deflation passageway, which allows the physician to precisely inflate and/or deflate the bulbs 115, 120 to match the patient's anatomical characteristics. Referring to FIG. 20, the internal module 200 includes a gastric or proximal end 245 with an end wall 250. When the device 100 is assembled, the internal module 200, namely the proximal end 245, is received by the downstream internal cavity 325 of the collar 310. Referring to FIGS. 16, 20, 29 and 30, the collar alignment members 333a, b reside radially outward of the periphery of the end wall 250 of the internal module 200. In some implementations, collar alignment features 333a, b improve the securement of the collar 310 and the internal module 200 due to their complementary shapes. Adhesives can also be used to further secure the collar 310 to the internal module 200 and such adhesives may be disposed between the collar alignment features 333a, b and the alignment surfaces 197 of the internal module 200.

The gastric portion 261 of the module 200 includes a plurality of longitudinal ribs 272, 274, 276, 278 integrally formed with and extending longitudinally along the gastric portion 261. The longitudinal ribs 272, 274, 276, 278 are radially spaced from each other around the periphery of the module 200. The longitudinal ribs 272, 274, 276, 278 are preferably tubular and define internal channels 272a, 274a, 276a, 278a, respectively. The ribs 274, 278 are offset or spaced a distance from the end wall 250, wherein a first recessed gap 245a is formed in the gastric portion 261 adjacent the onset of the rib 274 and a second recessed gap 245b is formed in the gastric portion 261 adjacent the onset of the rib 278. The ribs 274, 278 extend from the gaps 245a, b towards the intermediate module portion 262 but their distal ends terminate at the intermediate portion 262. As a result, the channels 274a, 278a do not extend past the intermediate portion 262. The recessed gap 245a forms an extent of the first inflation passageway 204, and the recessed gap 245b forms an extent of the first deflation passageway 208. The first recessed gap 245a enables fluid communication between the gastric bulb 115 and the inflation valve 316, while the second recessed gap 245b enables fluid communication between the gastric bulb 115 and the deflation valve 320. The ribs 274, 278 do not provide any functional aspects for inflation and/or deflation of the gastric bulb 115, however, they reduce asymmetric weight distributions and structurally balance the device 100, and reduce bending, bowing and/or flexing of various elements of the inflatable weight control device 100, particularly the internal module 200.

The ribs 272, 276 extend from the end wall 250 longitudinally through the gastric portion 261 to the intermediate portion 262, however, the internal channels 272a, 276a extend through the intermediate portion 262 to the duodenal portion 263 of the module 200. Because the internal channels 272a, 276a extend through an internal region of the intermediate portion 262, the outer surface 262a of the intermediate portion 262 is preferably devoid of external protrusions. The duodenal portion 263 of the module 200 includes exposed longitudinal channels 282, 284, 286, 288 that are shown as being recessed into the duodenal portion 263. Alternatively, the duodenal portion 263 includes ribs with a distal end opening and that form internal channels like those found in the gastric portion 261. The exposed channels 282, 286 extend from the intermediate portion 262 along a substantial extent of the length of the duodenal portion 263. In the embodiment of the Figures, the channels 282, 286 extend the entire length of the duodenal portion 263 and reach the distal end 264. The channels 282, 286 are in fluid communication with the internal channels 272a, 276a that extend from the gastric portion 261 and through the intermediate portion 262. The internal channel 272a and the exposed channel 282 form an extent of the first inflation passageway 202 that enables fluid communication between the duodenal bulb 120 and the inflation valve 314. The internal channel 276a and the exposed channel 286 form an extent of the first deflation passageway 206 that enables fluid communication between the duodenal bulb 120 and the deflation valve 318. The exposed channels 284, 288 do not provide any functional aspects for inflation and/or deflation of the duodenal bulb 120, however, they reduce asymmetric weight distributions and structurally balance the device 100, and reduce bending, bowing and/or flexing of various elements of the inflatable weight control device 100, particularly the internal module 200.

Figure 27:
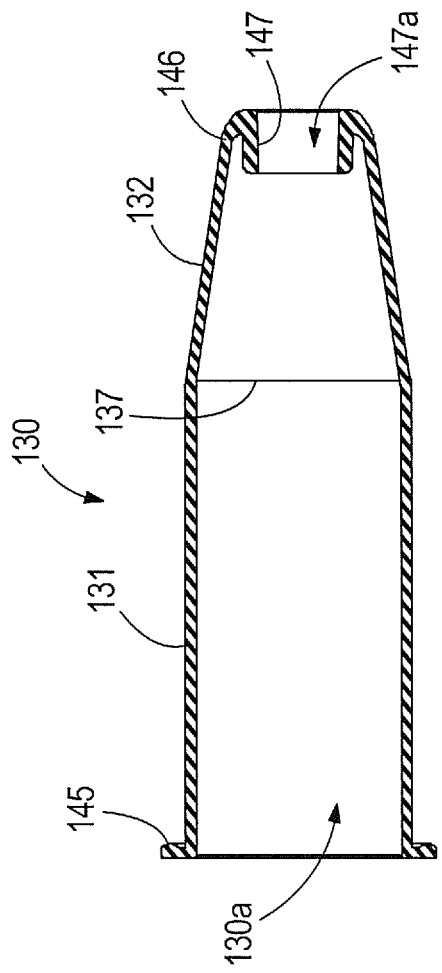
FIG. 27 is a sectional view taken along line 27 of FIG. 26.
Figure 26:
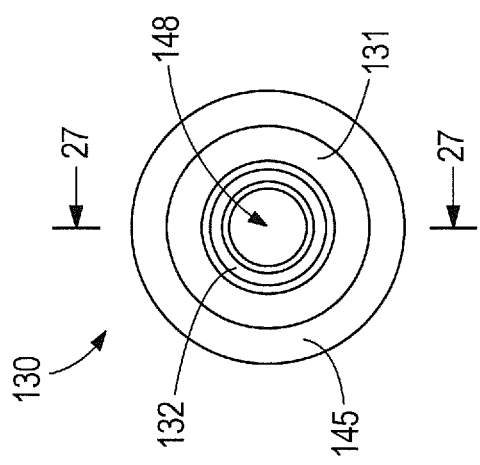
FIG. 26 is a front view of the inflatable body of FIG. 24.

FIGS. 24-27 show various views of the inflatable bladder or member 130 that defines an internal cavity 140 that is configured to receive the internal module 200. Referring to FIGS. 27, 29 and 30, the inflatable bladder 130 defines an internal cavity 130a and has a tapered distal end 146 with an inwardly directed internal flange 147 that extends into the distal end 264 of the module 200 and is secured to the duodenal portion 263 of the internal module 200. As shown in FIG. 27, the flange 147 is defined by a substantially parallel wall arrangement. A major segment 131 of the bladder 130 has a substantially linear configuration, while a minor segment 132 of the bladder 130 has a tapered configuration leading to the distal end 146. The major segment 131 comprises a majority of the length of the bladder 130 while the minor segment 132 comprises a minority of that length. As a result of the tapered configuration, the cross-section of the minor segment 132 is reduced along the length of the segment 132 from the major segment 131 to the distal end 146. A circumferential boundary 137, such as a groove, separates the majority and minor segments 131, 132. When the device 100 is assembled (see e.g., FIGS. 29 and 30), the internal flange 147 defines a distal opening 148 that is aligned with the lumen 205 of the internal module 200. Referring to FIGS. 32 and 33, for example, the minor bladder segment 132 overlies the duodenal portion 263 of the module 200 including the inflation and deflation passageways 202, 206. The majority bladder segment 130 overlies both the intermediate portion 202 and the gastric portion 261 of the module 200 including the inflation and deflation passageways 202, 204, 206, 208. As shown in FIGS. 29 and 30, for example, an intermediate portion 125 of the majority bladder segment 131 is secured to the intermediate portion 202 of the internal module 200 by at least one reinforcing bands 165. The inflatable bladder 130 has a peripheral mounting flange 145 at the gastric end of the majority segment 131 that is secured to the collar 310 by at least one retaining ring 155. In addition, an adhesive may be used to further secure the bladder 130 to the module 200 and/or the collar 310. The inflatable bladder 130 may be formed from a single flexible material having the same flexibility or rigidity throughout, a single flexible material having portions with different flexibilities or rigidities, or multiple materials coupled or bonded together. For example, the material for the portion of the inflatable bladder 130 that corresponds to the intermediate portion 125 may have less flexibility or more rigidity than the portions of the inflatable bladder 130 that correspond with the first and second bulbs 115, 120.

Turning now to FIG. 28, a rear view of the weight control device 100 is shown with the fill tube assembly 55 attached. FIG. 29 is a cross section taken along line 29 of FIG. 28, while FIG. 30 shows a cross section taken along line 30 of FIG. 28. As shown in FIGS. 29 and 30, the inflatable bladder 130 connects to the internal module 200 at multiple locations. The intermediate portion 125 of the inflatable bladder 130 is connected to the intermediate portion 262 of the internal module 200. For instance, an adhesive may be used to connect the inflatable bladder 130 to the intermediate portion 262 of the internal module 200. Additionally, the inflatable bladder 130 is connected to a duodenal portion 263 of the internal module 200 by a distal end cap 390 having a cylindrical segment 395 that extends into both the inflatable bladder 130, at its distal end 146, and the distal end 264 of the duodenal module portion 263. The cylindrical segment 395 of the distal end cap 390 defines a central opening that is aligned with the internal passageway 235. As shown in FIGS. 29 and 30, a flange 391 extends radially outward from the cylindrical segment 395 and externally abuts the distal end 146 of the bladder 130. An adhesive may also be used to secure the inflatable bladder 130 to the distal end cap 390 and distal end 264 of the internal module 200. As shown in FIGS. 29 and 30, the distal end 264 of the duodenal module portion 263 has a reduced thickness that defines a mating finger 264a that engages an exterior surface of the internal bladder flange 147. In this manner, the bladder flange 147 is positioned between the cylindrical segment 395 of the distal end cap 390 and the mating finger 264a in the assembled position and when the device 100 is implanted in the patient.

The connection of the inflatable bladder 130 to the internal module 200 at these regions restricts the areas of the weight control device 100 that may expand when the inflation fluid is supplied to the weight control device 100, whereby the inflatable bladder 130 inflates only at the first bladder portion 113 and the second bladder portion 118 to form the first bulb 115 and the second bulb 120, respectively. One or more circumferential reinforcing bands 165 may be used to further restrict the intermediate portion 125 from expanding when the inflation fluid is supplied to the weight control device 100. The reinforcing bands 165 may be attached to the intermediate portion 125 by any suitable means, such as by an adhesive, ultrasonic welding, silicone overmolding or a heat shrinkable tube, for example. In some embodiments, the adhesive used is MED2-4213 Fast-Cure Silicone Adhesive produced by NuSil. Further, the MED2-4213 adhesive can be used to adhere any two or more elements of the inflatable weight control device 100 together. The reinforcing bands 165 are configured to constrict a portion of the inflatable bladder 130 within a receiving area 265, that can be a channel or depression, formed in an outer extent of the internal module 200. The reinforcing bands 165 transform some or all of the peel force on the intermediate portion 125 to a tensile force in the reinforcing bands' 165 circumferential direction. The reinforcing bands 165 have a high tensile strength that helps to prevent circumferential elongation of the intermediate portion 125 of the device 100, thus helping to prevent peeling or delamination of the inflatable bladder 130 from the intermediate portion 262 of the internal module 200. In some embodiments, the intermediate portion 262 has a length of 1.5-4.0 cms, preferably 2.5-3.5 cms, and most preferably 3.0 cms, to facilitate proper placement and maintenance of the intermediate portion 125 in the pyloric valve 86 while also maintaining a slight offset of the first and second bulbs 115, 120 from the valve 86.

The peripheral flange 145 of the inflatable bladder 130 is secured to an inner wall 311 of the collar 310 of the valve body assembly 300. The flange 145 may be secured to the inner wall 311 by any suitable means, such as by an adhesive, for example. The flange 145 may be alternatively or further secured by a retaining ring 155. The retaining ring 155 allows an adhesive to be applied to both sides of the flange 145 when the retaining ring 155 and flange 145 are connected by an adhesive, allowing the flange to be placed in double shear (e.g., glued on both sides). A rib can also be formed on the flange 145 to provide a rigid mounting surface for the retaining ring 155. The retaining ring 155 also prevents the first bulb 115 from applying a pure peel type force to the flange 145 by providing a radial/centripetal (e.g., towards the center) counter balance to the centrifugal (e.g., away from the center) forces of the inflatable bladder 130 when inflated. The remaining internal tension of the inflatable bladder 130, after frictional losses, acts to pull the flange 145 towards the center, creating a nearly pure double shear force type loading on the flange 145, which is a strong bond direction of the adhesive joint. The retaining ring 155 further provides an additional barrier between the fluid used to fill the first bulb 115 and the external volume of the stomach 90 (e.g., stomach acid). The retaining ring 155 is also, in some embodiments, connected to the collar 310 by an adhesive.

The internal module 200 comprises a substantially rigid material (such as polyethereherketone ("PEEK")) that resists bending and deflection within a patient. The rigid material assist the central lumen 205 in resisting this deformation which facilitates the internal passageway 235 staying open to allow chyme to flow therethrough. The intermediate portion 262 of the internal passageway has the largest outer diameter of the internal module 200, thereby allowing a gap or cavity to exist between the inflatable bladder 130 and the gastric and duodenal portions 261, 263 of the module 200. It is the provision of the inflation fluid to both of these areas that results in the formation of the first and second inflated bulbs 115, 120. As shown in FIGS. 29 and 30, the weight control device 100 is generally symmetric about a longitudinal axis passing through the internal passageway 235. This symmetry allows the weight control device 100 to be implanted within the patient without having to angularly align the weight control device 100 within the pylorus 70.

Figure 31:
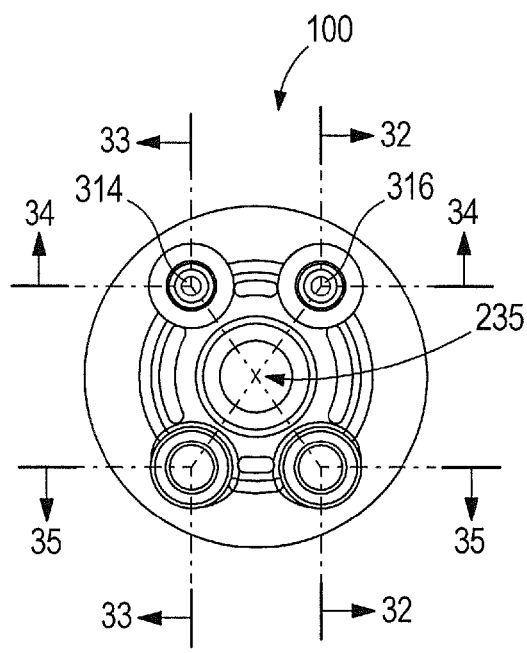
FIG. 31 is a rear view of the weight control device in a deflated state.

Due to its unique components, including the inflation and deflation fluid passageways 202, 204, 206, 208, the extent or amount of inflation of the first and second bulbs 115, 120 provided by the physician that implants the device 100 can be precisely tailored to the patient's anatomical requirements. FIG. 31 is an end view of a proximal end of the weight control device 100 in a deflated state without any inflation tubes attached. FIG. 32 is a cross section of the weight control device 100 taken along line 32 of FIG. 31, wherein the section plane exposes the first inflation and deflation passageways 204, 208. In general, the first inflation passageway 204 extends through the internal module 200 and the first gap 245 to provide working fluid to inflate the gastric or first bulb 115. Specifically, the first inflation passageway 204 has an initial or proximal end adjacent to the valve body assembly 300 to provide fluid communication to the first bulb 115. Fluid passes through a second inflation valve 316 of the valve body 300, flows through the first inflation passageway 204 and the first gap 245a, and then fills the narrow, circumferential cavity C1 between the gastric module portion 261 and the inflatable bladder 130 to inflate the first bulb 115. Similarly, the first deflation passageway 208 is in fluid communication with and extends from the first bulb 115 through the gap 245b and the internal module 200 to the valve body assembly 300. A second deflation valve 320 is also provided to control the flow of fluid from the first bulb 115 when the weight control device 100 is being deflated, such as when the device 100 is being adjusted or removed from a patient. The second deflation valve 320 can be opened with a tool or needle to allow working fluid to flow from the first inflation portion 115 past the second deflation valve 320 to the exterior of the inflatable weight control device 100. Because the ribs 274, 278 are sealed, the internal channels 274, 278 appear to define a rectangular void in FIG. 32.

FIG. 33 is a cross section taken along line 33 of FIG. 31, wherein the section plane exposes the second inflation and deflation passageways 202, 206. In general, the second inflation passageway 202 extends from the valve body assembly 300 through the gastric and intermediate portions 261, 262 of the module 200 to provide working fluid to inflate the duodenal or second bulb 120. Specifically, the second inflation passageway 202 has an initial or proximal end adjacent to the valve body assembly 300 to provide fluid communication to the second bulb 120. Fluid passes through a first inflation valve 314 of the valve body assembly 300, flows through the second inflation passageway 202 (which includes the internal channel 272a and the exposed channel 282) and then fills the narrow, circumferential cavity C2 between the duodenal module portion 263 and the inflatable bladder 130 to inflate the second bulb 120. Similarly, the second deflation passageway 206 also extends through the module 200 to provide fluid communication with the second bulb 120. Specifically, the second deflation passageway 206 extends from the second bulb 120, through the gastric and intermediate portions 261, 262 of the module 200 to the valve body assembly 300. A first deflation valve 318 is also provided to control the flow of fluid from the second bulb 120 when the weight control device 100 is being deflated, such as for adjustment or removal from a patient. The first deflation valve 318 can be opened with a tool operatively associated with an endoscope to allow working fluid to flow from the second bulb 120 past the first deflation valve 318 to the exterior of the weight control device 100.

FIG. 34 is a cross section of the weight control device 100 taken along line 34 of FIG. 31, wherein the section plane exposes the second inflation passageway 202 and the first inflation passageway 204. Like numerals and structures shown in FIGS. 34, 35 and 37-40 correspond to, and function in the same way as, like numerals and structures shown in previous figures. In some implementations, the second inflation passageway 202 is longer than the first inflation passageway 204. FIG. 35 is a cross section of the weight control device 100 taken along line 35 of FIG. 31. In some implementations of the device 100, the second deflation passageway 206 is longer than the first deflation passageway 208. The lengths of the inflation and deflation passageways are a function of the orientation of the first and second bulbs 115, 120 with respect to the valve body assembly 300, which is a common starting point for the passageways. Plugs 460, 462 prevent fluid flow through the first deflation valve 318 and the second deflation valve 320, respectively, to the exterior of the inflatable weight control device 100. In some embodiments, plugs 460, 462 also receive a disposable needle which can be used to allow working fluid to exit the inflatable weight control device 100 through the needle, or to forcibly open the first and second deflation valves 318, 320.

Turning now to FIG. 36, an end view of a proximal end of the weight control device 100 in the inflated position is shown. The first inflation bulb 115 is clearly visible at the proximal end of the weight control device 100. FIG. 37 is a cross section of the weight control device 100 in an inflated state taken along line 37 of FIG. 36. As shown in FIG. 37, the first bulb 115 has a greater diameter than the second bulb 120. The first inflation passageway 204 and the first deflation passageway 208 extend from the valve body assembly 300 to provide for inflation and deflation, respectively, of the first bulb 115. The first inflation passageway 204 extends through the internal module 200 and the first gap 245 to provide working fluid to inflate the gastric or first bulb 115. Specifically, the first inflation passageway 204 has an initial or proximal end adjacent to the valve body assembly 300 to provide fluid communication to the first bulb 115. Fluid passes through a second inflation valve 316 of the valve body 300, flows through the first inflation passageway 204 and the first gap 245a, and then fills the narrow, circumferential cavity C1 between the gastric module portion 261 and the inflatable bladder 130 to inflate the first bulb 115. The second inflation passageway 202 extends from the valve body assembly 300 through the gastric and intermediate portions 261, 262 of the module 200 to provide working fluid to inflate the duodenal or second bulb 120. Specifically, the second inflation passageway 202 has an initial or proximal end adjacent to the valve body assembly 300 to provide fluid communication to the second bulb 120. Fluid passes through a first inflation valve 314 of the valve body assembly 300, flows through the second inflation passageway 202 (which includes the internal channel 272a and the exposed channel 282) and then fills the narrow, circumferential cavity C2 between the duodenal module portion 263 and the inflatable bladder 130 to inflate the second bulb 120. FIG. 38 is a cross section of the weight control device 100 taken along line 38 of FIG. 36. The second inflation passageway 202 and the second deflation passageway 206 extend from the valve body assembly 300 past a midpoint of the internal module 200 and provide for inflation and deflation, respectively, of the second inflation bulb 120.

Figure 40:
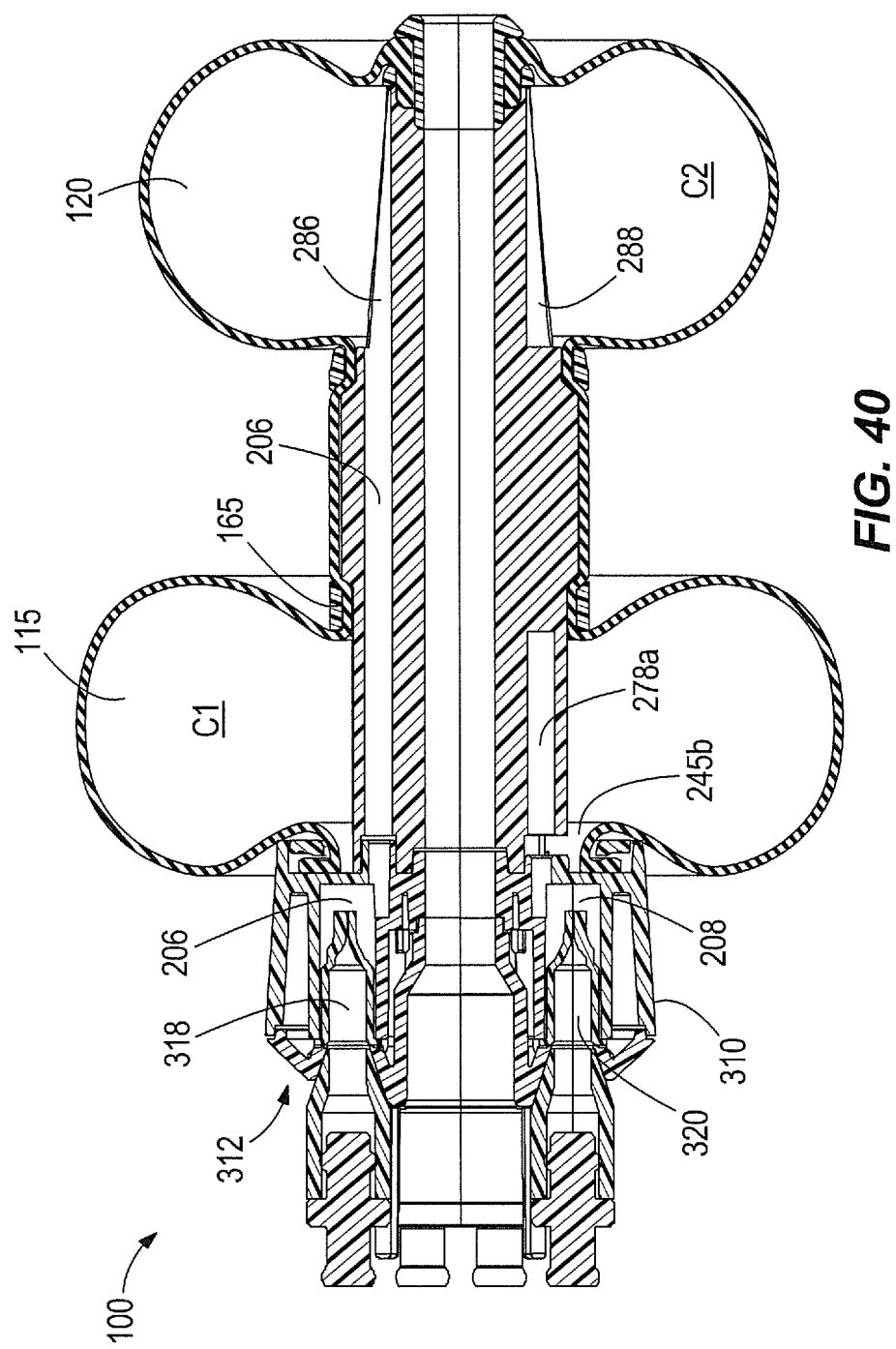
FIG. 40 is a sectional view taken along line 40 of FIG. 36.

FIG. 39 is a cross section of the weight control device 100 taken along line 39 of FIG. 36. The second inflation passageway 202 leading to the second inflation bulb 120 and the first inflation passageway 204 leading to the first inflation bulb 115 are shown. The second inflation passageway 202 and the first inflation passageway 204 open at generally normal directions to each other to provide fluid to the first inflation bulb 115 and the second inflation bulb 120, respectively. FIG. 40 is a cross section of the weight control device 100 taken along line 40 of FIG. 36, and showing the second deflation passageway 206 leading to the second inflation bulb 120 and the first deflation passageway 208 leading to the first inflation bulb 115. The second deflation passageway 206 and the first deflation passageway 208 open at generally normal directions to each other to remove fluid from the first inflation bulb 115 and the second inflation bulb 120.

As shown in FIGS. 37-40, when a sufficient amount of inflation fluid is supplied, the inflatable bladder 130 is displaced away from the internal module 200 in the areas of the first bulb 115 and the second bulb 120. However, the inflatable bladder 130 is not displaced at its intermediate portion 125 because the inflatable bladder 130 is attached to the waist portion 262 of the internal module 200, in some embodiments by an adhesive. The nose of the inflatable bladder 130 is also attached to the internal module 200 at the distal end 264. The connection of the inflatable bladder 130 to the distal end 264 further secures the inflatable bladder 130 to the internal module 200, but also helps define the shape of the second inflation bulb 120. The second inflation bulb 120 is therefore disposed between the distal end 264, the distal end cap 390 and the waist portion 262 of the internal module 200. The flange 145 of the inflatable bladder 130 is also attached to the valve body assembly 300 at the inner wall 311 proximate a distal ledge 360. The first inflation bulb 115 is disposed between the distal ledge 360 of the valve body assembly 300 and the waist portion 262 of the internal module 200. As shown in FIGS. 37-40 the inflatable bladder 130 is attached to substantially the entire waist portion 262 of the internal module 200. The valve body assembly 300 is attached to the internal module 200 before the inflatable bladder 130 is attached. For example, the collar 310 of the valve body assembly 300 may be attached using an adhesive to connect the collar 310 to a proximal end 245 of the internal module 200.

In use, the weight control device 100 is implanted endoscopically into a patient in a deflated state such that the intermediate portion 125 is within the pylorus 70, and generally near the pylorus valve or pylorus sphincter 86. Once positioned, inflation fluid, such as saline, oil or air, is provided from the fill tube assembly 55 through the first valve 314 to the second inflation passageway 202 to the second bulb 120. Similarly, fluid from the fill tube assembly 55 is provided through the second valve 316 to the first inflation passageway 204 to the first bulb 115. The fluid causes the first bulb 115 and the second bulb 120 to expand so that the weight control device 100 is within the pylorus 70 and restricts the flow of chyme from the stomach 90 into the duodenum 80. For example, the weight control device 100 may be configured so that chyme may flow from the stomach 90 into the duodenum 80 through the internal passageway 235 and around the external surfaces of the weight control device 100, both flows occurring at a reduced rate to induce satiety in the patient. This feature allows for the transfer of chyme into the duodenum 80 even if the internal passageway 235 becomes blocked or occluded. As another example, the weight control device 100 may be configured so that chyme may only flow from the stomach 90 into the duodenum 80 through the internal passageway 235 of the weight control device 100. Custom adjustment of each of the first and second bulbs 115, 120 is feasible due to the dedicated pairing of an inflation and deflation passageway 202, 204, 206, 208 with a first or second bulbs 115, 120 respectively.

It is contemplated that the size of the internal passageway 235 may vary based upon the patient. For instance, if the patient has been utilizing some type of weight control device, like weight control device 100 for a period of time, a subsequent weight control device would have an internal passageway that has a smaller diameter to allow less chyme to pass through the subsequent weight control device, promoting additional weight loss within the patient. Alternatively, an insert may be placed into the internal passageway 235 of the weight control device 100 to reduce the diameter of an opening that chyme may pass through, thereby encouraging additional weight loss within the patient.

Numerous modifications may be made to the foregoing disclosure without departing from the basic teachings thereof. Although the present disclosure has been described in substantial detail with reference to one or more specific embodiments, those of skill in the art will recognize that changes may be made thereto without departing from the scope and spirit of the disclosure.

What is claimed is:

1. An endoscopically implantable weight control device that forms a partial gastric outlet obstruction in a patient's digestive tract to promote early and prolonged satiety in the patient, the weight control device comprising:
    an elongated internal module having a gastric portion, a tapered duodenal portion with a distal end, and an intermediate portion positioned between the gastric and duodenal portions, the internal module also having a central lumen extending through the gastric, duodenal and intermediate portions;
    a valve body assembly connected to a gastric end of the internal module, the valve body having a central aperture, a first set of an inflation valve and a deflation valve and a second set of an inflation valve and a deflation valve, wherein said first and second sets of valves are arranged radially about the central aperture;
    an inflatable member that receives the internal member and that is joined to only (i) the valve body assembly, (ii) the intermediate portion of the internal module and (iii) the distal end of the internal module,
    the inflatable member having (i) a major segment that has a linear configuration and that overlies the gastric and intermediate portions of the internal module and (ii) a minor segment that has a tapered configuration and that overlies the duodenal portion of the internal module;
    wherein when the inflatable member is supplied with a working fluid (i) a gastric bulb is formed in the inflatable member, said gastric bulb residing between the valve body assembly and the intermediate portion of the internal module, and (ii) a duodenal bulb in the inflatable member, said duodenal bulb residing between the intermediate portion of the internal module and the distal end of the internal module;
    wherein the valve body assembly and the internal module include both a first inflation passageway and a first deflation passageway for the transport of the working fluid to the gastric bulb, wherein the gastric bulb forms a partial gastric outlet obstruction when the weight control device is implanted in the patient;
    wherein the valve body assembly and the internal module include both a second inflation passageway and a second deflation passageway for the transport of the working fluid to the duodenal bulb, wherein the second inflation and deflation passageways extend through the gastric and intermediate portions of the internal module to reach the duodenal portion of the internal module; and,
    wherein the central lumen of the internal module and the central aperture of the valve body assembly are cooperatively aligned to provide an internal passageway extending through the weight control device that receives and allows for the passage of chyme from the patient's stomach through the device to the duodenum.

2. The implantable weight control device of claim 1, wherein a proximal end of the major segment of the inflatable member includes a flange that is secured to the valve body assembly by a retaining ring.

3. The implantable weight control device of claim 1, further comprising at least one reinforcing band disposed on an exterior surface of the intermediate portion of the inflatable member.

4. The implantable weight control device of claim 3, wherein the intermediate portion of the internal module is not inflated and resides within the patient's pyloric valve when the device is implanted in the patient.

5. The implantable weight control device of claim 1, wherein the gastric portion of the internal module includes a first pair of longitudinal ribs that are offset a distance from an end wall of said internal module and extend towards the intermediate portion of the internal module.

6. The implantable weight control device of claim 5, wherein the first pair of longitudinal ribs define recessed gaps in said gastric portion, wherein the gaps form an extent of said first inflation and deflation passageways for the transport of the working fluid to the gastric bulb.

7. The implantable weight control device of claim 5, wherein the first pair of longitudinal ribs terminate at the intermediate portion of the internal module.

8. The implantable weight control device of claim 5, wherein the gastric portion of the internal module includes a second pair of longitudinal ribs that extend from an end wall of said internal module and through both the intermediate portion and duodenal portion of said internal module.

9. The implantable weight control device of claim 8, wherein the second pair of longitudinal ribs define internal channels that extend across the gastric portion and through the intermediate portion of the internal module.

10. The implantable weight control device of claim 9, wherein the duodenal portion of the internal module includes a pair of exposed channels that extend from the intermediate portion towards the distal end of the internal module.

11. The implantable weight control device of claim 10, wherein said exposed channels are in fluid communication with said internal channels to form an extent of the second inflation and deflation passageways for the transport of the working fluid to the duodenal bulb.

12. The implantable weight control device of claim 10, wherein the central lumen of the internal module has a substantially constant internal diameter along its length.

13. The implantable weight control device of claim 1, wherein the minor segment of the inflatable member includes a distal end with an inwardly directed flange that extends into the distal end of the internal module and is secured to the duodenal portion of the internal module.

14. The implantable weight control device of claim 13, wherein the distal end of the duodenal portion of the internal module has a reduced thickness that define a mating finger that engages the inwardly directed flange of the distal end of the inflatable member.

15. The implantable weight control device of claim 13, further comprising a cap that extends into both the flange of the inflatable member and the distal end of the internal module to further secure the inflatable member to the internal module.

16. The implantable weight control device of claim 15, wherein the cap includes a cylindrical segment that extends into both the flange of the inflatable member and the distal end of the internal module, the cylindrical segment defining a central opening that is aligned with said internal passageway that extends through the weight control device.

17. The implantable weight control device of claim 1, wherein the valve body assembly further comprises a collar and an end cap, the collar residing between the end cap and the internal module, and wherein both sets of inflation and deflations valves being disposed between the collar and the end cap.

18. The implantable weight control device of claim 17, wherein the collar includes tubular valve stems that receive both sets of inflation and deflation valves.

19. The implantable weight control device of claim 17, wherein the collar includes a plurality flow channels arranged about said central aperture and extending from an inner collar wall towards the internal module, wherein the flow channels are fluid communication with the first and second sets of inflation and deflation valves.

20. The implantable weight control device of claim 17, wherein a plurality of projections extend from an outer wall of the end cap, the projections configured to be engaged by an endoscope, to facilitate insertion of the weight control device into the patient or removal of the weight control device from the patient.

21. The implantable weight control device of claim 20, wherein the projections are arranged about the central aperture of the valve body assembly.

22. The implantable weight control device of claim 17, wherein the end cap includes a plurality of apertures arranged about the central aperture of the valve body assembly, each aperture being cooperatively aligned with one valve from the sets of inflation and deflation valves.

23. The weight control device of claim 17, wherein the end cap includes a central bushing surrounding the central aperture that projects into an internal cavity of the collar to facilitate engagement of the end cap and the collar.

* * * * *